(12) United States Patent
Vafai et al.

(10) Patent No.: US 11,147,982 B1
(45) Date of Patent: Oct. 19, 2021

(54) METHOD AND SYSTEM FOR THERMAL STIMULATION OF TARGETED NEURAL CIRCUITS FOR NEURODEGENERATIVE DISORDERS

(71) Applicant: KAMBIX INNOVATIONS, LLC, Albuquerque, NM (US)

(72) Inventors: Kambiz Vafai, Mission Viejo, CA (US); Erfan Kosari, Irvine, CA (US)

(73) Assignee: Kambix Innovations, LLC, Albuquerque, NM (US)

(*) Notice: Subject to any disclaimer, the term of this patent is extended or adjusted under 35 U.S.C. 154(b) by 0 days.

(21) Appl. No.: 17/334,032

(22) Filed: May 28, 2021

Related U.S. Application Data

(60) Provisional application No. 63/184,436, filed on May 5, 2021.

(51) Int. Cl.
| | | |
|---|---|---|
| *A61N 2/04* | (2006.01) | |
| *A61N 2/02* | (2006.01) | |
| *A61B 18/04* | (2006.01) | |
| *A61N 2/00* | (2006.01) | |
| *A61N 2/12* | (2006.01) | |

(52) U.S. Cl.
CPC .............. *A61N 2/006* (2013.01); *A61N 2/12* (2013.01)

(58) Field of Classification Search
CPC ................ A61N 2/006; A61N 1/36025; A61N 2007/0026; A61N 1/36053; A61N 5/0622; A61N 1/36021; A61N 1/36082; A61N 2/02; A61N 2/008; A61N 1/36067; A61N 1/36075; A61N 1/36078; A61N 1/36085; A61N 1/36096; A61N 1/36167
See application file for complete search history.

(56) References Cited

U.S. PATENT DOCUMENTS

| | | | |
|---|---|---|---|
| 9,427,585 B2 | 8/2016 | Gliner | |
| 9,492,680 B2 | 11/2016 | Lu | |
| 10,526,383 B2 | 1/2020 | Mintz | |
| 10,776,453 B2 | 9/2020 | Fallon et al. | |
| 10,933,243 B2 | 3/2021 | Senderowicz et al. | |
| 10,953,017 B2 | 3/2021 | Grimaldi et al. | |

(Continued)

OTHER PUBLICATIONS

"Theoretical Analysis for Wireless Magnetothermal Deep Brain Stimulation Using Commercial Nanoparticles." Le TA, Bui MP, Yoon J. 2019. Int J. Mol.Sci. 20(12), 2873 (Year: 2019).*

(Continued)

*Primary Examiner* — Christine H Matthews
*Assistant Examiner* — Joshua Daryl D Lannu
(74) *Attorney, Agent, or Firm* — Ortiz & Lopez, PLLC; Kermit D. Lopez; Luis M. Ortiz

(57) ABSTRACT

A method and system for noninvasively treating a neurodegenerative disorder, can involve determining characteristics indicative of physical attributes of a central nervous system, the characteristics including parameters for diminishing adverse impacts of a magnetothermal stimulation treatment for a neurodegenerative disorder with respect to the central nervous system, and applying as a part of the magnetothermal stimulation treatment and based on the characteristics of the physical attributes of the central nervous system, a magnetic field to the brain for a thermal stimulation of neuron cells within the brain.

20 Claims, 11 Drawing Sheets

(56) References Cited

U.S. PATENT DOCUMENTS

| | | | |
|---|---|---|---|
| 2001/0031906 A1* | 10/2001 | Ishikawa | A61N 2/02 600/13 |
| 2004/0078056 A1* | 4/2004 | Zangen | A61N 2/02 607/2 |
| 2005/0182288 A1* | 8/2005 | Zabara | A61N 2/006 600/14 |
| 2006/0199992 A1* | 9/2006 | Eisenberg | A61N 2/006 600/14 |
| 2012/0065700 A1 | 3/2012 | Gliner | |
| 2020/0246179 A1* | 8/2020 | Peyman | A61K 9/127 |
| 2020/0286620 A1 | 9/2020 | Fallon et al. | |

OTHER PUBLICATIONS

A.R.A. Khaled, K. Vafai, Optimization modeling of analyte adhesion over an inclined microcantilever-based biosensor, J. Micromech. Microeng. 14 (8) (2004) 1220, doi: 10.1088/0960-1317/14/8/015.

S. Chung, K. Vafai, Mechanobiology of low-density lipoprotein transport within an arterial wall—Impact of hyperthermia and coupling effects, J. Biomech. 47 (1) (2014) 137-147, doi: 10.1016/j.jbiomech.2013.09.030.

S. Mahjoob, K. Vafai, N. Reginald Beer, Rapid microfluidic thermal cycler for polymerase chain reaction nucleic acid amplification, Int. J. Heat Mass Transf. 51 (9-10) (2008) 2109-2122, doi: 10.1016/j.ijheatmasstransfer.2007.11.014.

I. Osorio, F.-C. Chang, N. Gopalsami, Seizure control with thermal energy? Modeling of heat diffusivity in brain tissue and computer-based design of a prototype minicooler, Epilepsy Behav. 16 (2) (2009) 203-211, doi: 10.1016/j.yebeh.2009.08.014.

G.A.M. Pop, D.J. Duncker, M. Gardien, P. Vranckx, S. Versluis, D. Hasan, C.J. Slager, The clinical significance of whole blood viscosity in (cardio) vascular medicine, Neth. Heart J. 10 (12) (2002) 512.

A. Dittmar, T. Pauchard, G. Delhomme, E. Vernet-Maury, A thermal conductivity sensor for the measurement of skin blood flow, Sens. Actuators B Chem. 7 (1-3) (1992) 327-331, doi: 10.1016/0925-4005(92)80318-R.

S.A. Sapareto, L.E. Hopwood, W.C. Dewey, M.R. Raju, J.W. Gray, Effects of hyperthermia on survival and progression of Chinese hamster ovary cells, Cancer Res. 38 (2) (1978) 393-400.

Z. Qin, S.K. Balasubramanian, W.F. Wolkers, J.A. Pearce, J.C. Bischof, Correlated parameter fit of Arrhenius model for thermal denaturation of proteins and cells, Ann. Biomed. Eng. 42 (12) (2014) 2392-2404, doi: 10.1007/s10439-014-1100-y.

C.J. Diederich, Thermal ablation and high-temperature thermal therapy: overview of technology and clinical implementation, Int. J. Hyperth. 21 (8) (2005) 745-753, doi: 10.1080/02656730500271692.

M. Raoof, C. Zhu, W.D. Kaluarachchi, S.A. Curley, Luciferase-based protein denaturation assay for quantification of radiofrequency field-induced targeted hyperthermia: developing an intracellular thermometer, Int. J. Hyperth. 28 (3) (2012) 202-209, doi: 10.3109/02656736.2012.666318.

I.A. Chang, Considerations for thermal injury analysis for RF ablation devices, Open Biomed. Eng. J. 4 (2010) 3, doi: 10.2174/2F1874120701004020003.

G.C. Van Rhoon, T. Samaras, P.S. Yarmolenko, M.W. Dewhirst, E. Neufeld, N. Kuster, CEM43° C. thermal dose thresholds: a potential guide for magnetic resonance radiofrequency exposure levels? Eur. Radiol. 23 (8) (2013) 2215-2227, doi: 10.1007/s00330-013-2825-y.

J.P. Yung, A. Shetty, A. Elliott, J.S. Weinberg, R.J. McNichols, A. Gowda, J.D. Hazle, R. Jason Stafford, Quantitative comparison of thermal dose models in normal canine brain, Med. Phys. 37 (10) (2010) 5313-5321, doi: 10.1118/1.3490085.

F. Pelaez, N. Manuchehrabadi, P. Roy, H. Natesan, Y. Wang, E. Racila, H. Fong, et al., Biomaterial scaffolds for non-invasive focal hyperthermia as a potential tool to ablate metastatic cancer cells, Biomaterials 166 (2018) 27-37, doi: 10.1016/j.biomaterials.2018.02.048.

D. Schlesinger, M. Lee, G. Ter Haar, B. Sela, M. Eames, J. Snell, N. Kassell, J. Sheehan, J.M. Larner, J.-.F. Aubry, Equivalence of cell survival data for radiation dose and thermal dose in ablative treatments: analysis applied to essential tremor thalamotomy by focused ultrasound and gamma knife, Int. J. Hyperth. 33 (4) (2017) 401-410, doi: 10.1080/02656736.2016.1278281.

N. Barnat, A. Grisey, B. Lecuelle, J. Anquez, B. Gerold, S. Yon, J.F. Aubry, Noninvasive vascular occlusion with HIFU for venous insufficiency treatment: preclinical feasibility experience in rabbits, Phys. Med. Biol. 64 (2) (2019) 025003, doi: 10.1088/1361-6560/aaf58d.

R.J. McNichols, A. Gowda, M. Kangasniemi, J.A. Bankson, R.E. Price, J.D. Hazle, MR thermometry-based feedback control of laser interstitial thermal therapy at 980nm, Lasers Surg. Med. Off. J. Am. Soc. Laser Med. Surg. 34 (1) (2004) 48-55, doi: 10.1002/lsm.10243.

Manual, Abaqus Scripting User'S. Abaqus Jun. 11, 2011. http://130.149 89,No. 2080: v6.

D. Jain, A. Mukherjee, N. Kwatra, Local micromechanics of moisture diffusion in fiber reinforced polymer composites, Int. J. Heat Mass Transf. 76 (2014) 199-209, doi: 10.1016/j.ijheatmasstransfer.2014.04.031.

L. Han, M. Neumann, Effect of dimensionality on the Nelder-Mead simplex method, Optim. Methods Softw. 21 (1) (2006) 1-16, doi: 10.1080/10556780512331318290.

A. Bhowmik, R. Singh, R. Repaka, S.C. Mishra, Conventional and newly developed bioheat transport models in vascularized tissues: a review, J. Therm. Biol. 38 (3) (2013) 107-125, doi: 10.1016/j.jtherbio.2012.12.003.

A. Bousselham, O. Bouattane, M. Youssfi, A. Raihani, 3D brain tumor localization and parameter estimation using thermographic approach on GPU, J. Therm. Biol. 71 (2018) 52-61, doi: 10.1016/j.jtherbio.2017.10.014.

M. Sadeghi-Goughari, A. Mojra, S. Sadeghi, Parameter estimation of brain tumors using intraoperative thermal imaging based on artificial tactile sensing in conjunction with artificial neural network, J. Phys. D Appl. Phys. 49 (7) (2016) 075404, doi: 10.1088/0022-3727/49/7/075404.

A. Bhowmik, R. Repaka, Estimation of growth features and thermophysical properties of melanoma within 3-D human skin using genetic algorithm and simulated annealing, Int. J. Heat Mass Transf. 98 (2016) 81-95, doi: 10.1016/i.ijheatmasstransfer.2016.03.020.

E. Kosari, K. Vafai, Thermal tissue damage analysis for magnetothermal neuromodulation and lesion size minimization, Brain Multiphys. (2020) 100014. https://doi.org/10.1016/j.brain.2020.100014.

W. Zahra, S.N. Rai, H. Birla, S.S. Singh, H. Dilnashin, A.S. Rathore, S.P. Singh, The global economic impact of neurodegenerative diseases: Opportunities and challenges, in: Bioeconomy for Sustainable Development, Springer, Singapore, 2020, pp. 333-345. https://doi.org/10.1007/978-981-13-9431-7_17.

S.A. Stanley, J.E. Gagner, S. Damanpour, M. Yoshida, J.S. Dordick, J.M. Friedman, Radio-wave heating of iron oxide nanoparticles can regulate plasma glucose in mice, Science 336 (6081) (2012) 604-608. https://doi.org/10.1126/science.1216753.

R. Munshi, S.M. Qadri, Q. Zhang, I.C. Rubio, P. Del Pino, A. Pralle, Magnetothermal genetic deep brain stimulation of motor behaviors in awake, freely moving mice, Elife 6 (2017), e27069. https://doi.org/10.7554/eLife.27069.

A. Wong, Y. Mao, A. Levy, J. Rothstein, D. Bergles, P.C. Searson, The blood-brain barrier: an engineering perspective, Front. Neuroeng. 6 (2013) 7. https://doi.org/10. 3389/fneng.2013.00007.

T. Dalkara, Y. Gursoy-Ozdemir, M. Yemisci, Brain microvascular pericytes in health and disease, Acta Neuropathol. 122 (1) (2011) 1. https://doi.org/10.1007/s00401-011-0847-6.

C. Iadecola, Neurovascular regulation in the normal brain and in Alzheimer's disease, Nat. Rev. Neurosci. 5 (5) (2004) 347-360. https://doi.org/10.1038/nrn1387.

N. Wattiez, C. Constans, T. Deffieux, P.M. Daye, M. Tanter, J.-F. Aubry, P. Pouget, Transcranial ultrasonic stimulation modulates single-neuron discharge in macaques performing an antisaccade task, Brain Stimul. 10 (6) (2017) 1024-1031. https://doi.org/10.1016/j.brs.2017.07.007.

(56) References Cited

OTHER PUBLICATIONS

R.F. Dallapiazza, K.F. Timbie, S. Holmberg, J. Gatesman, M.B. Lopes, R.J. Price, G.W. Miller, W.J. Elias, Noninvasive neuromodulation and thalamic mapping with low-intensity focused ultrasound, J. Neurosurg. 128 (3) (2017) 875-884. https://doi.org/10.3171/2016.11.JNS16976.

F.U. Amin, A.K. Hoshiar, T.D. Do, Y. Noh, S.A. Shah, M.S. Khan, J. Yoon, M.O. Kim, Osmotin-loaded magnetic nanoparticles with electromagnetic guidance for the treatment of Alzheimer's disease, Nanoscale 9 (30) (2017) 10619-10632. https://doi.org/10.1039/C7NR00772H.

G. Nagel, D. Ollig, M. Fuhrmann, S. Kateriya, A.M. Musti, E. Bamberg, P. Hegemann, Channelrhodopsin-1: a light-gated proton channel in green algae, Science 296 (5577) (2002) 2395-2398. https://doi.org/10.1126/science.1072068.

G. Nagel, T. Szellas, W. Huhn, S. Kateriya, N. Adeishvili, P. Berthold, D. Ollig, P. Hegemann, E. Bamberg, Channelrhodopsin-2, a directly light-gated cation-selective membrane channel, Proc. Natl. Acad. Sci. U. S. A. 100 (24) (2003) 13940-13945. https://doi.org/10.1073/pnas.1936192100.

M.G. Christiansen, A.W. Senko, P. Anikeeva, Magnetic strategies for nervous system control, Annu. Rev. Neurosci. 42 (2019) 271-293. https://doi.org/10.1146/annurevneuro-070918-050241.

R. Chen, G. Romero, M.G. Christiansen, A. Mohr, P. Anikeeva, Wireless magnetothermal deep brain stimulation, Science 347 (6229) (2015) 1477-1480. https://doi.org/10.1126/science.1261821.

M. Roet, S.-A. Hescham, A. Jahanshahi, B.P.F. Rutten, P.O. Anikeeva, Y. Temel, Progress in neuromodulation of the brain: a role for magnetic nanoparticles? Prog. Neurobiol. 177 (2019) 1-14. https://doi.org/10.1016/j.pneurobio.2019.03.002.

A. Cervadoro, C. Giverso, R. Pande, S. Sarangi, L. Preziosi, J. Wosik, A. Brazdeikis, P. Decuzzi, Design maps for the hyperthermic treatment of tumors with superparamagnetic nanoparticles, PLoS One 8 (2) (2013) e57332. https://doi.org/10.1371/journal.pone.0057332.

K. Maier-Hauff, R. Rothe, R. Scholz, U. Gneveckow, P. Wust, B. Thiesen, A. Feussner, et al., Intracranial thermotherapy using magnetic nanoparticles combined with external beam radiotherapy: results of a feasibility study on patients with glioblastoma multiforme, J. Neurooncol 81 (1) (2007) 53-60. https://doi.org/10.1007/s11060-006-9195-0.

E. Evans, Y.-C. Fung, Improved measurements of the erythrocyte geometry, Microvasc. Res. 4 (4) (1972) 335-347. https://doi.org/10.1016/0026-2862(72)90069-6.

F. Janoschek, Mesoscopic Simulation of Blood and General Suspensions in Flow, 2013. https://doi.org/10.6100/ir761379.

H.L. Goldsmith, R. Skalak, Hemodynamics, Annu. Rev. Fluid Mech. 7 (1) (1975) 213-247.

C.K. Aidun, J.R. Clausen, Lattice-Boltzmann method for complex flows, Annu. Rev. FluidMech. 42 (2010) 439-472. https://doi.org/10.1146/annurev-fluid-121108-145519.

G. Karniadakis, A. Beskok, N. Aluru, Microflows and Nanoflows: Fundamentals and Simulation, vol. 29, Springer Science & Business Media, 2006.

L. Talbot, R.K. Cheng, R.W. Schefer, D.R. Willis, Thermophoresis of particles in a heated boundary layer, J. Fluid Mech. 101 (1979) 737-758.

A.F. Smith, V. Doyeux, M. Berg, M. Peyrounette, M. Haft-Javaherian, A.-E. Larue, J.H. Slater, et al., Brain capillary networks across species: a few simple organizational requirements are sufficient to reproduce both structure and function, Front. Physiol. 10 (2019) 233. https://doi.org/10.3389/fphys.2019.00233.

M. Peyrounette, Y. Davit, M. Quintard, S. Lorthois, Multiscale modelling of blood flow in cerebral microcirculation: details at capillary scale control accuracy at the level of the cortex, PLoS One 13 (1) (2018) e0189474. https://doi.org/10.1371/journal.pone.0189474.

J.S. Marshall, S. Li, Adhesive Particle Flow, Cambridge University Press, 2014.

J.J. Wade, K. Breslin, K.F. Wong-Lin, J. Harkin, B. Flanagan, H. Van Zalinge, S. Hall, et al., Calcium microdomain formation at the perisynaptic cradle due toNCXreversal: a computational study, Front. Cell. Neurosci. 13 (2019) 185. https://doi.org/10.3389/fncel.2019.00185.

T.A. Glaze, S. Lewis, S. Bahar, Chimera states in a Hodgkin-Huxley model of thermally sensitive neurons, Chaos 26 (8) (2016) 083119. https://doi.org/10.1063/1.4961122.

D. Bini, C. Cherubini, S. Filippi, On vortices heating biological excitable media, Chaos, Solitons Fractals 42 (4) (2009) 2057-2066. https://doi.org/10.1016/j.chaos.2009.03.164.

Y.G. Lv, Theoretical evaluation on monitoring hypothermic anesthesia by the electrical response of human skin neurons, Forsch. Ingenieurwes. 71 (2) (2007) 79-88. https://doi.org/10.1007/s10010-006-0046-0.

A.L. Hodgkin, A.F. Huxley, A quantitative description of membrane current and its application to conduction and excitation in nerve, J. Physiol. 117 (4) (1952) 500. https://doi.org/10.1113/jphysiol.1952.sp004764.

Y.-g. Lv, J. Liu, Interpretation on thermal comfort mechanisms of human bodies by combining Hodgkin-Huxley neuron model and Pennes bioheat equation, Forsch. Ingenieurwes. 69 (2) (2005) 101-114. https://doi.org/10.1007/s10010-004-0145-8.

J.G. Nicholls, A.R. Martin, B.G. Wallace, P.A. Fuchs, From Neuron to Brain, vol. 271, Sinauer Associates, Sunderland, MA, 2001.

S.H. Kim, H. Pitsch, I.D. Boyd, Accuracy of higher-order lattice Boltzmann methods for microscale flows with finite Knudsen numbers, J. Comput. Phys. 227 (19) (2008) 8655-8671. https://doi.org/10.1016/j.jcp.2008.06.012.

S. Chien, Shear dependence of effective cell volume as a determinant of blood viscosity, Science 168 (3934) (1970) 977-979. https://doi.org/10.1126/science.168.3934.977, Abstract.

Louiza Bohn Thomsen, Thomas Linemann, Svend Birkelund, Gitte Abildgaard Tarp, and Torben Moos; "Evaluation of Targeted Delivery to the Brain Using Magnetic Immunoliposomes and Magnetic Force", Materials 2019, 12, 3576; doi:10.3390/ma12213576; www.mdpi.com/journal/materials.

Louiza Bohn Thomsen, Maj Schneider Thomsen and Torben Moos; "Targeted drug delivery to the brain using magnetic nanoparticles", Ther. Deliv. (2015) 6(10), 1145-1155.

P. Martinez-Martin, M. Dendy, Y.J. Jalundhwala, F. Mu, E. Ohashi, T. Marshall, K. Sail, The long-term direct and indirect economic burden among Parkinson's disease caregivers in the United States, Mov. Disord. 34 (2) (2019) 236-245, doi: 10.1002/mds.27579.

S.L. Kowal, T.M. Dall, R. Chakrabarti, M.V. Storm, A. Jain, The current and projected economic burden of Parkinson's disease in the United States, Mov. Disord. 28 (3) (2013) 311-318, doi: 10.1002/mds.25292.

S.V. Zaichick, K.M. McGrath, G. Caraveo, The role of Ca2 + signaling in Parkinson's disease, Dis. Model. Mech. 5 (10) (2017) 519-535, doi: 10.1242/dmm.028738.

S.A. Stanley, J.E. Gagner, S. Damanpour, M. Yoshida, J.S. Dordick, J.M. Friedman, Radio-wave heating of iron oxide nanoparticles can regulate plasma glucose in mice, Science 336 (6081) (2012) 604-608, doi: 10.1126/science.1216753.

Deep-Brain Stimulation for Parkinson's Disease Study Group, Deep-brain stimulation of the subthalamic nucleus or the pars interna of the globus pallidus in Parkinson's disease, N. Engl. J. Med. 345 (13) (2001) 956-963, doi: 10.1056/NEJMoa000827.

M. Roet, S.-A. Hescham, A. Jahanshahi, B.PF Rutten, P.O. Anikeeva, Y. Temel, Progress in neuromodulation of the brain; a role for magnetic nanoparticles? Prog. Neurobiol. (2019), doi: 10.1016/j.pneurobio.2019.03.002.

M.-R. Kim, J.Y. Yun, B. Jeon, Y.H. Lim, K.R. Kim, H.-J. Yang, S.H. Paek, Patients' reluctance to undergo deep brain stimulation for Parkinson's disease, Park. Relat. Disord. 23 (2016) 91-94, doi: 10.1016/j.parkreldis.2015.11.010.

L. Verhagen, C. Gallea, D. Folloni, C. Constans, D.E. Jensen, H. Ahnine, L. Roumazeilles, et al., Offline impact of transcranial focused ultrasound on cortical activation in primates, Elife 8 (2019) e40541, doi: 10.7554/eLife.40541.

N. Wattiez, C. Constans, T. Deffieux, P.M. Daye, M. Tanter, J.-F. Aubry, P. Pouget, Transcranial ultrasonic stimulation modulates

(56) References Cited

OTHER PUBLICATIONS single-neuron discharge in macaques performing an antisaccade task, Brain Stimul. 10 (6) (2017) 1024-1031, doi: 10.1016/j.brs.2017.07.007.

R.F. Dallapiazza, K.F. Timbie, S. Holmberg, J. Gatesman, M. Beatriz Lopes, R.J. Price, G. Wilson Miller, W. Jeffrey Elias, Noninvasive neuromodulation and thalamic mapping with low-intensity focused ultrasound, J. Neurosurg. 128 (3) (2017) 875-884, doi: 10.3171/2016.11.JNS16976.

R. Munshi, S.M. Qadri, Q. Zhang, I.C. Rubio, P. del Pino, A. Pralle, Magnetothermal genetic deep brain stimulation of motor behaviors in awake, freely moving mice, Elife 6 (2017) e27069, doi: 10.7554/eLife.27069.

F.U. Amin, A.K. Hoshiar, T.D. Do, Y. Noh, S.A. Shah, M.S. Khan, J. Yoon, M.O. Kim, Osmotin-loaded magnetic nanoparticles with electromagnetic guidance for the treatment of Alzheimer's disease, Nanoscale 9 (30) (2017) 10619-10632, doi: 10.1039/C7NR00772H.

G. Nagel, T. Szellas, W. Huhn, S. Kateriya, N. Adeishvili, P. Berthold, D. Ollig, P. Hegemann, E. Bamberg, Channelrhodopsin-2, a directly light-gated cationselective membrane channel, Proc. Natl. Acad. Sci. 100 (24) (2003) 13940-13945, doi: 10.1073/pnas.1936192100.

G. Nagel, D. Ollig, M. Fuhrmann, S. Kateriya, A.M. Musti, E. Bamberg, P. Hegemann, Channelrhodopsin-1: a light-gated proton channel in green algae, Science 296 (5577) (2002) 2395-2398, doi: 10.1126/science.1072068.

K. Deisseroth, Optogenetics: 10 years of microbial opsins in neuroscience, Nat. Neurosci.18 (9) (2015) 1213, doi: 10.1038/nn.4091.

R. Chen, G. Romero, M.G. Christiansen, A. Mohr, P. Anikeeva, Wireless magnetothermal deep brain stimulation, Science 347 (6229) (2015) 1477-1480, doi: 10.1126/science.1261821.

R. Munshi, S.M. Qadri, A. Pralle, Transient magnetothermal neuronal silencing using the chloride channel anoctamin1 (TMEM16A), Front. Neurosci. 12 (2018) 560, doi: 10.3389/fnins.2018.00560.

J.-H. Lee, J.-W. Kim, M. Levy, A. Kao, S.-H. Noh, D. Bozovic, J. Cheon, Magnetic nanoparticles for ultrafast mechanical control of inner ear hair cells, ACS Nano 8 (7) (2014) 6590-6598, doi: 10.1021/nn5020616.

R.J. Mannix, S. Kumar, F. Cassiola, M. Montoya-Zavala, E. Feinstein, M. Prentiss, D.E. Ingber, Nanomagnetic actuation of receptor-mediated signal transduction, Nat. Nanotechnol. 3 (1) (2008) 36, doi: 10.1038/nnano.2007.418.

H.X. Nguyen, N. Bursac, Ion channel engineering for modulation and de novo generation of electrical excitability, Curr. Opin. Biotechnol. 58 (2019) 100-107, doi: 10.1016/j.copbio.2019.01.004.

M.G. Christiansen, A.W. Senko, P. Anikeeva, Magnetic strategies for nervous system control, Annu. Rev. Neurosci. 42 (2019), doi: 10.1146/annurev-neuro-070918-050241.

C. Petters, E. Irrsack, M. Koch, R. Dringen, Uptake and metabolism of iron oxide nanoparticles in brain cells, Neurochem. Res. 39 (9) (2014) 1648-1660, doi: 10.1007/s11064-014-1380-5.

S.V. Spirou, M. Basini, A. Lascialfari, C. Sangregorio, C. Innocenti, Magnetic hyperthermia and radiation therapy: radiobiological principles and current practice, Nanomaterials 8 (6) (2018) 401, doi: 10.3390/nano8060401.

F.KH Van Landeghem, K. Maier-Hauff, A. Jordan, K.-T. Hoffmann, U. Gneveckow, R. Scholz, B. Thiesen, W. Brück, A. von Deimling, Post-mortem studies in glioblastoma patients treated with thermotherapy using magnetic nanoparticles, Biomaterials 30 (1) (2009) 52-57, doi: 10.1016/j.biomaterials.2008.09.044.

M. Tominaga, M.J. Caterina, A.B. Malmberg, T.A. Rosen, H. Gilbert, K. Skinner, B.E. Raumann, A.I. Basbaum, D. Julius, The cloned capsaicin receptor integrates multiple pain-producing stimuli, Neuron 21 (3) (1998) 531-543, doi: 10.1016/S0896-6273(00)80564-4.

A. Cervadoro, C. Giverso, R. Pande, S. Sarangi, L. Preziosi, J. Wosik, A. Brazdeikis, P. Decuzzi, Design maps for the hyperthermic treatment of tumors with superparamagnetic nanoparticles, PLoS One 8 (2) (2013) e57332, doi: 10.1371/journal.pone.0057332.

K. Maier-Hauff, R. Rothe, R. Scholz, U. Gneveckow, P. Wust, B. Thiesen, A. Feussner, et al., Intracranial thermotherapy using magnetic nanoparticles combined with external beam radiotherapy: results of a feasibility study on patients with glioblastoma multiforme, J. Neurooncol. 81 (1) (2007) 53-60, doi: 10.1007/s11060-006-9195-0.

R. Chen, M.G. Christiansen, P. Anikeeva, Maximizing hysteretic losses in magnetic ferrite nanoparticles via model-driven synthesis and materials optimization, ACS Nano 7 (10) (2013) 8990-9000, doi: 10.1021/nn4035266.

C. Constans, P. Mateo, M. Tanter, J.-F. Aubry, Potential impact of thermal effects during ultrasonic neurostimulation: retrospective numerical estimation of temperature elevation in seven rodent setups, Phys. Med. Biol. 63 (2) (2018) 025003, doi: 10.1088/1361-6560/aaa15c.

W.J. Elias, M. Khaled, J.D. Hilliard, J.-F. Aubry, R.C. Frysinger, J.P. Sheehan, M. Wintermark, M.B. Lopes, A magnetic resonance imaging, histological, and dose modeling comparison of focused ultrasound, radiofrequency, and Gamma Knife radiosurgery lesions in swine thalamus, J. Neurosurg. 119 (2) (2013) 307-317, doi: 10.3171/2013.5.JNS122327.

K. Wang, F. Tavakkoli, S. Wang, K. Vafai, Analysis and analytical characterization of bioheat transfer during radiofrequency ablation, J. Biomech. 48 (6) (2015) 930-940, doi: 10.1016/j.jbiomech.2015.02.023.

M. Iasiello, K. Vafai, A. Andreozzi, N. Bianco, Low-density lipoprotein transport through an arterial wall under hyperthermia and hypertension conditions—an analytical solution, J. Biomech. 49 (2) (2016) 193-204, doi: 10.1016/j.jbiomech.2015.12.015.

P. Keangin, K. Vafai, P. Rattanadecho, Electromagnetic field effects on biological materials, Int. J. Heat Mass Transf. 65 (2013) 389-399, doi: 10.1016/j.ijheatmasstransfer.2013.06.039.

H.H. Pennes, Analysis of tissue and arterial blood temperatures in the resting human forearm, J. Appl. Physiol. 1 (2) (1948) 93-122, doi: 10.1152/jappl.1948.1.2.93.

P.K. Gupta, J. Singh, K.N. Rai, Numerical simulation for heat transfer in tissues during thermal therapy, J. Therm. Biol. 35 (6) (2010) 295-301, doi: 10.1016/j.jtherbio.2010.06.007.

R. Goyal, K. Vafai, Electromagnetic field-induced thermal management of biological materials, Numer. Heat Transf. Part A Appl. 72 (4) (2017) 275-290, doi: 10.1080/10407782.2017.1372672.

A.L. Sukstanskii, D.A. Yablonskiy, Theoretical model of temperature regulation in the brain during changes in functional activity, Proc. Natl. Acad. Sci. 103 (32) (2006) 12144-12149, doi: 10.1073/pnas.0604376103.

R. Goyal, R. Bhargava, FEM simulation of EM field effect on body tissues with bionanofluid (blood with nanoparticles) for nanoparticle mediated hyperthermia, Math. Biosci. 300 (2018) 76-86, doi: 10.1016/j.mbs.2018.03.016.

H. Huang, S. Delikanli, H. Zeng, D.M. Ferkey, A. Pralle, Remote control of ion channels and neurons through magnetic-field heating of nanoparticles, Nat. Nanotechnol. 5 (8) (2010) 602-606, doi: 10.1038/NNANO.2010.125.

J.R. Lepock, Cellular effects of hyperthermia: relevance to the minimum dose for thermal damage, Int. J. Hyperth. 19 (3) (2003) 252-266, doi: 10.1080/0265673031000065042.

S. Chen, A.Z. Weitemier, X. Zeng, L. He, X. Wang, Y. Tao, A.JY Huang, et al., Nearinfrared deep brain stimulation via upconversion nanoparticle-mediated optogenetics, Science 359 (6376) (2018) 679-684, doi: 10.1126/science.aaq1144.

A. Nacev, C. Beni, O. Bruno, B. Shapiro, The behaviors of ferromagnetic nanoparticles in and around blood vessels under applied magnetic fields, J. Magn. Magn. Mater. 323 (6) (2011) 651-668, doi: 10.1016/j.immm.2010.09.008.

K. Khanafer, K. Vafai, A. Kangarlu, Water diffusion in biomedical systems as related to magnetic resonance imaging, Magn. Reson. Imaging 21 (1) (2003) 17-31, doi: 10.1016/S0730-725X(02)00632-X.

S.I. Abdelsalam, K. Vafai, Particulate suspension effect on peristaltically induced unsteady pulsatile flow in a narrow artery: blood flow model, Math. Biosci. 283 (2017) 91-105, doi: 10.1016/j.mbs.2016.11.012.

(56) References Cited

OTHER PUBLICATIONS

A.-.R.A. Khaled, K. Vafai, Analysis of oscillatory flow disturbances and thermal characteristics inside fluidic cells due to fluid leakage and wall slip conditions, J. Biomech. 37 (5) (2004) 721-729, doi: 10.1016/j.jbiomech.2003.09.017.
M. Shafahi, K. Vafai, Biofilm affected characteristics of porous structures, Int. J. Heat Mass Transf. 52 (3-4) (2009) 574-581, doi: 10.1016/j.ijheatmasstransfer.2008.07.013.
M. Iasiello, K. Vafai, A. Andreozzi, N. Bianco, Hypo- and hyperthermia effects on LDL deposition in a curved artery, Comput. Therm. Sci. Int. J. 11 (1-2) (2019), doi: 10.1615/ComputThermalScien.2018024754.
S. Shin, S.-W. Lee, K. Yun-Hee, Measurements of blood viscosity using a pressurescanning slit viscometer, KSME Int. J. 18 (6) (2004) 1036-1041.
R. Fahraeus, T. Lindqvist, The viscosity of the blood in narrow capillary tubes, Am. J. Physiol.-Leg. Content 96 (3) (1931) 562-568.
H.-j. Lim, Y.-J. Lee, J.-H. Nam, S. Chung, S. Shin, Temperature-dependent threshold shear stress of red blood cell aggregation, J. Biomech. 43 (3) (2010) 546-550. https://doi.org/10.1016/j.jbiomech.2009.09.031.
D.M. Eckmann, S. Bowers, M. Stecker, A.T. Cheung, Hematocrit, volume expander, temperature, and shear rate effects on blood viscosity, Anesth. Analg. 91 (3) (2000) 539-545. https://doi.org/10.1213/00000539-200009000-00007.
S.J. Hund, M.V. Kameneva, J.F. Antaki, A quasi-mechanistic mathematical representation for blood viscosity, Fluids 2 (1) (2017) 10. https://doi.org/10.3390/fluids2010010.
A. Sequeira, J. Janela, An overview of some mathematical models of blood rheology, in: A Portrait of State-of-the-Art Research at the Technical University of Lisbon, Springer, Dordrecht, 2007, pp. 65-87.
M. Iasiello, K. Vafai, A. Andreozzi, N. Bianco, Analysis of non-Newtonian effects on low-density lipoprotein accumulation in an artery, J. Biomech. 49 (9) (2016) 1437-1446. https://doi.org/10.1016/j.jbiomech.2016.03.017.
A. Nacev, C. Beni, O. Bruno, B. Shapiro, The behaviors of ferromagnetic nanoparticles in and around blood vessels under applied magnetic fields, J. Magn. Magn. Mater. 323 (6) (2011) 651-668. https://doi.org/10.1016/j.jmmm.2010.09.008.
T.P. Santisakultarm, N.R. Cornelius, N. Nishimura, A.I. Schafer, R.T. Silver, P.C. Doerschuk, W.L. Olbricht, C.B. Schaffer, In vivo two-photon excited fluorescence microscopy reveals cardiac- and respiration-dependent pulsatile blood flow in cortical blood vessels in mice, Am. J. Physiol. Heart Circ. Physiol. 302 (7) (2012) H1367-H1377. https://doi.org/10.1152/ajpheart.00417.2011.
Y.-c. Fung, Biomechanics: Motion, Flow, Stress, and Growth, Springer Science & Business Media, 2013.
S. Lorthois, F. Cassot, Fractal analysis of vascular networks: insights from morphogenesis, J. Theor. Biol. 262 (4) (2010) 614-633. https://doi.org/10.1016/j.jtbi.2009.10.037.
N. Nishimura, C.B. Schaffer, B. Friedman, P.D. Lyden, D. Kleinfeld, Penetrating arterioles are a bottleneck in the perfusion of neocortex, Proc. Natl. Acad. Sci. U. S. A. 104 (1) (2007) 365-370. https://doi.org/10.1073/pnas.0609551104.
A.S. Popel, P.C. Johnson, Microcirculation and hemorheology, Annu. Rev. Fluid Mech. 37 (2005) 43-69. https://doi.org/10.1146/annurev.fluid.37.042604.133933.
F. Cassot, F. Lauwers, C. Fouard, S. Prohaska, V. Lauwers-Cances, A novel threedimensional computer-assisted method for a quantitative study of microvascular networks of the human cerebral cortex, Microcirculation 13 (1) (2006) 1-18. https://doi.org/10.1080/10739680500383407.
B. Thomas, K.S. Sumam, Blood flow in human arterial system—a review, Procedia Technol. 24 (2016) 339-346. https://doi.org/10.1016/j.protcy.2016.05.045.
P. Eslami, J. Tran, Z. Jin, J. Karady, R. Sotoodeh, M.T. Lu, U. Hoffmann, A. Marsden, Effect of wall elasticity on hemodynamics and wall shear stress in patient-specific simulations in the coronary arteries, J. Biomech. Eng. 142 (2) (2020). https://doi.org/10.1115/1.4043722.
H. Sarin, Physiologic upper limits of pore size of different blood capillary types and another perspective on the dual pore theory of microvascular permeability, J. Angiogenes. Res. 2 (1) (2010) 14. https://doi.org/10.1186/2040-2384-2-14.
G. Li, M.J. Simon, L.M. Cancel, Z.-D. Shi, X. Ji, J.M. Tarbell, B. Morrison, M.F. Bingmei, Permeability of endothelial and astrocyte cocultures: in vitro blood-brain barrier models for drug delivery studies, Ann. Biomed. Eng. 38 (8) (2010) 2499-2511. https://doi.org/10.1007/s10439-010-0023-5.
L.M. Cancel, K. Arias, M. Bikson, J.M. Tarbell, Direct current stimulation of endothelial monolayers induces a transient and reversible increase in transport due to the electroosmotic effect, Sci. Rep. 8 (1) (2018) 1-13. https://doi.org/10.1038/s41598-018-27524-9.
L.M. Cancel, J.M. Tarbell, The role of mitosis in LDL transport through cultured endothelial cell monolayers, Am. J. Physiol. Heart Circ. Physiol. 300 (3) (2011) H769-H776. https://doi.org/10.1152/ajpheart.00445.2010.
L.M. Cancel, A. Fitting, J.M. Tarbell, In vitro study of LDL transport under pressurized (convective) conditions, Am. J. Physiol. Heart Circ. Physiol. 293 (1) (2007) H126-H132. https://doi.org/10.1152/ajpheart.01188.2006.
H.K. Kimelberg, Water homeostasis in the brain: basic concepts, Neuroscience 129 (4) (2004) 851-860. https://doi.org/10.1016/j.neuroscience.2004.07.033.
P.J. Blanco, L.O. M€uller, J.D. Spence, Blood pressure gradients in cerebral arteries: a clue to pathogenesis of cerebral small vessel disease, Stroke Vasc. Neurol. 2 (3) (2017) 108-117. https://doi.org/10.1136/svn-2017-000087.
S. Wang, K. Vafai, Analysis of low density lipoprotein (LDL) transport within a curved artery, Ann. Biomed. Eng. 43 (7) (2015) 1571-1584. https://doi.org/10.1007/s10439-014-1219-x.
S. Chung, K. Vafai, Mechanobiology of low-density lipoprotein transport within an arterial wall—impact of hyperthermia and coupling effects, J. Biomech. 47 (1) (2014) 137-147. https://doi.org/10.1016/j.jbiomech.2013.09.030.
R. Chen, M.G. Christiansen, P. Anikeeva, Maximizing hysteretic losses in magnetic ferrite nanoparticles via model-driven synthesis and materials optimization, ACS Nano 7 (10) (2013) 8990-9000. https://doi.org/10.1021/nn4035266.
M. Campisi, Y. Shin, T. Osaki, C. Hajal, V. Chiono, R.D. Kamm, 3D self-organized microvascular model of the human blood-brain barrier with endothelial cells, pericytes and astrocytes, Biomaterials 180 (2018) 117-129. https://doi.org/10.1016/j.biomaterials.2018.07.014.
D. Rosenfeld, A.W. Senko, J. Moon, I. Yick, G. Varnavides, D. Gregurec, F. Koehler, et al., Transgene-free remote magnetothermal regulation of adrenal hormones, Sci. Adv. 6 (15) (2020) eaaz3734. https://doi.org/10.1126/sciadv.aaz3734.
O. Mahian, L. Kolsi, M. Amani, P. Estelle, G. Ahmadi, C. Kleinstreuer, J.S. Marshall, et al., Recent advances in modeling and simulation of nanofluid flows—part I: fundamentals and theory, Phys. Rep. 790 (2019) 1-48. https://doi.org/10.1016/j.physrep.2018.11.004.
C.T. Crowe, J.D. Schwarzkopf, M. Sommerfeld, Y. Tsuji, Multiphase Flows With Droplets and Particles, CRC Press, 2011.
S. Elghobashi, On predicting particle-laden turbulent flows, Appl. Sci. Res. 52 (4) (1994) 309-329. https://doi.org/10.1007/BF00936835.
L.S. Sundar, M.K. Singh, A.C.M. Sousa, Investigation of thermal conductivity and viscosity of Fe3O4 nanofluid for heat transfer applications, Int. Commun. Heat Mass Transfer 44 (2013) 7-14. https://doi.org/10.1016/j.icheatmasstransfer.2013.02.014.
S.M. Vanaki, P. Ganesan, H.A. Mohammed, Numerical study of convective heat transfer of nanofluids: a review, Renew. Sustain. Energy Rev. 54 (2016) 1212-1239. https://doi.org/10.1016/j.rser.2015.10.042.
J.C. Maxwell, A Treatise on Electricity and Magnetism, vol. 1, Clarendon Press, 1873.
A.A. Minea, Uncertainties in modeling thermal conductivity of laminar forced convection heat transfer with water alumina nanofluids,

(56) References Cited

OTHER PUBLICATIONS

Int. Commun. Heat Mass Transfer 68 (2014) 78-84. https://doi.org/10.1016/j.ijheatmasstransfer.2013.09.018.

Z. Alloui, J. Guiet, P. Vasseur, M. Reggio, Natural convection of nanofluids in a shallow rectangular enclosure heated from the side, Can. J. Chem. Eng. 90 (1) (2012) 69-78. https://doi.org/10.1002/cjce.20523.

E. Abu-Nada, Effects of variable viscosity and thermal conductivity of Al2O3-water nanofluid on heat transfer enhancement in natural convection, Int. J. Heat Fluid Flow 30 (4) (2009) 679-690. https://doi.org/10.1016/j.ijheatfluidflow.2009.02.003.

R.L. Hamilton, O.K. Crosser, Thermal conductivity of heterogeneous twocomponent systems, Ind. Eng. Chem. Fundam. 1 (3) (1962) 187-191. https://doi.org/10.1021/i160003a005.

W. Yu, S.U.S. Choi, The role of interfacial layers in the enhanced thermal conductivity of nanofluids: a renovated Maxwell model, J. Nanopart. Res. 5 (1-2) (2003) 167-171. https://doi.org/10.1023/A:1024438603801.

M. Corcione, Empirical correlating equations for predicting the effective thermal conductivity and dynamic viscosity of nanofluids, Energ. Conver. Manage. 52 (1) (2011) 789-793. https://doi.org/10.1016/j.enconman.2010.06.072.

S. Hassani, R. Saidur, S. Mekhilef, A. Hepbasli, A new correlation for predicting the thermal conductivity of nanofluids; using dimensional analysis, Int. J. Heat Mass Transfer 90 (2015) 121-130. https://doi.org/10.1016/j.ijheatmasstransfer.2015.06.040.

H.C. Brinkman, The viscosity of concentrated suspensions and solutions, J. Chem. Phys. 20 (4) (1952) 571. https://doi.org/10.1063/1.1700493.

A. Einstein, On the theory of the Brownian movement, Ann. Phys. 19 (4) (1906) 371-381.

M.H. Esfe, S. Saedodin, S. Wongwises, D. Toghraie, An experimental study on the effect of diameter on thermal conductivity and dynamic viscosity of Fe/water nanofluids, J. Therm. Anal. Calorim. 119 (3) (2015) 1817-1824. https://doi.org/10.1007/s10973-014-4328-8.

S.U.S. Choi, J.A. Eastman, Enhancing Thermal Conductivity of Fluids With Nanoparticles. No. ANL/MSD/CP-84938; CONF-951135-29, Argonne National Lab., IL (United States), 1995.

A. Albojamal, K. Vafai, Analysis of single phase, discrete and mixture models, in predicting nanofluid transport, Int. J. Heat Mass Transf. 114 (2017) 225-237. https://doi.org/10.1016/j.ijheatmasstransfer.2017.06.030.

S. Rashidi, J.A. Esfahani, R. Ellahi, Convective heat transfer and particle motion in an obstructed duct with two side by side obstacles by means of DPM model, Appl. Sci. 7 (4) (2017) 431. https://doi.org/10.3390/app7040431.

E. Matijevic, Medical Applications of Colloids, Springer-Verlag New York, 2008.

P.G.T. Saffman, The lift on a small sphere in a slow shear flow, J. Fluid Mech. 22 (2) (1965) 385-400. https://doi.org/10.1017/s0022112065000824.

A. Li, G. Ahmadi, Dispersion and deposition of spherical particles from point sources in a turbulent channel flow, Aerosol Sci. Tech. 16 (4) (1992) 209-226. https://doi.org/10.1080/02786829208959550.

\* cited by examiner

METHOD AND SYSTEM FOR THERMAL STIMULATION OF TARGETED NEURAL CIRCUITS FOR NEURODEGENERATIVE DISORDERS

CROSS REFERENCE TO PROVISIONAL APPLICATION

This patent application claims priority under 35 U.S.C. § 119 to U.S. Provisional Patent Application Ser. No. 63/184,436 entitled "Method and System for Thermal Stimulation of Targeted Neural Circuits for Neurodenerative Disorders," which was filed on May 5, 2020, and is incorporated by reference herein in its entirety.

TECHNICAL FIELD

Embodiments are related to medical treatments and neurosurgical procedures for treating and ameliorating neurodegenerative disorders such as Alzheimer's disease and Parkinson's disease. Embodiments further relate to the thermal stimulation of targeted neural circuits for the medical treatment of neurodegenerative disorders.

BACKGROUND

The worldwide incidence of neurodegenerative disorders primarily affects patients that are mid to late life and is anticipated to soar owing to the growth in the elderly population. The major associated financial burden is allocated to first, Alzheimer's disease (AD) and second, Parkinson's disease (PD). For instance, in the US, the treatment expenses incurred by PD patients is approximately USD 14.4 billion per year. As the population grows, it is expected that the expenses will double by 2040. A failure to achieve a promising therapy to these kinds of disorders without noninvasive impacts might poses a huge threat to the public health.

Parkinson's disease (PD) is a chronic and progressive degenerative disease of the brain that impairs motor control, speech, and other functions. The disease is named after English physician James Parkinson, who gave a detailed description of it in an 1817 work titled, "An Essay on the Shaking Palsy".

Parkinson's disease belongs to a group of conditions called movement disorders. It is characterized by muscle rigidity, resting tremor (typically at about 5 Hz), slowing of movement (bradykinesia) and, in extreme cases, nearly complete loss of movement (akinesia). Secondary symptoms may include high-level cognitive dysfunction, subtle language problems, and depression.

A conventional therapy for Parkinson's is called Deep Brain Stimulation (DBS) that involves implanting electrodes within certain areas of the brain. These electrodes can produce electrical impulses that can regulate abnormal impulses. The dangerous side effects of DBS, however, such as risk of bleeding and infection, has motivated scientists to propose a minimally invasive treatment, termed as "Thermal stimulation" or "Thermal neuromodulation" by direct injection onto the extracellular space (ECS).

Thermal stimulation can employ a magnetic field, such as an alternating magnetic field (AMF) to excite magnetic nanoparticles (MNP) of which they are directly injected to the midbrain. The nanoparticles exposed to the magnetic field can dissipate heat via thermal stimulation (hysteresis). The local elevated temperature activates a type of heat-sensitive ion-channel known as TRPV1, which leads to calcium cation influx. The calcium cation influx can eventually propagate signals in neurons, which can activate neuronal networks and ameliorate the symptoms of the neurodegenerative disorder (e.g., symptoms of Parkinson's disease, Alzheimer's disease, etc). In a magnetothermal neuromodulation treatment, a primary aim is to attain a minimum temperature that may be required for stimulation which is 43° C. and maintain the tissue temperature below 50° C. to avoid thermal cytotoxic impacts.

Hence, neurosurgical operations may seek thermo engineering theories to alleviate the risk levels and effectively administer the remote therapy. To date, however, these thermal cytotoxic issues have remained a problem with magnetothermal neuromodulation treatments. This problem has not been adequately addressed. The present inventors believe the success and safety of magnetothermal neuromodulation treatments strongly relies on thermal interactions of the brain capillary wall with blood flow carrying heat dissipative nano-transducers.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for methods and systems for noninvasively treating a neurodegenerative disorder.

It is another aspect of the disclosed embodiments to provide methods and systems for determining characteristics indicative of physical attributes of a central nervous system and using these characteristics in the application of an alternating magnetic field to the brain for a thermal stimulation of neuron cells within the brain as a part of the magnetothermal stimulation treatment for a neurodegenerative disorder.

It is a further aspect of the disclosed embodiments to provide for the thermal stimulation of targeted neural circuits via remotely-controlled nano-transducers as part of a therapy for neurodegenerative disorders.

It is also an aspect of the disclosed embodiments to provide for thermal tissue damage analysis for magnetothermal neuromodulation and lesion size minimization for use as a part of a therapy for neurodegenerative disorders.

The aforementioned aspects and other objectives and advantages can now be achieved as described herein. In an embodiment, a method for noninvasively treating a neurodegenerative disorder, can involve: determining characteristics indicative of physical attributes of a central nervous system, the characteristics including parameters for diminishing adverse impacts of a magnetothermal stimulation treatment for a neurodegenerative disorder with respect to the central nervous system; and applying as a part of the magnetothermal stimulation treatment and based on the characteristics of the physical attributes of the central nervous system, a magnetic field to the brain for a thermal stimulation of neuron cells within the brain.

In an embodiment of the method, the characteristics indicative of the physical attributes can include blood flow dynamics.

In an embodiment of the method, the characteristics indicative of the physical attributes can include magnetic nanoparticle interactions with blood capillary flow.

In an embodiment of the method, the characteristics indicative of the physical attributes can include heat transfer across at least one area of the brain.

In an embodiment of the method, the characteristics indicative of the physical attributes can include regulated neural signaling.

In an embodiment of the method, the characteristics indicative of the physical attributes can include one or more of: blood flow dynamics, magnetic nanoparticle interactions with capillary flow, heat transfer, and regulated neural signaling.

An embodiment of the method can further involve injecting nanoparticles into brain capillaries of the brain prior to the applying of the magnetic field to the brain.

In an embodiment of the method, the characteristics indicative of the physical attributes can include temperature profiles within the central nervous system when exposed to the magnetic field.

An embodiment of the method can further involve calculating a brain tissue temperature distribution associated with the brain based on a finite element method.

In an embodiment of the method, the characteristics of the physical attributes can account for a movement of ions between presynaptic cradle and astrocyte soma under an influence of a temperature elevation included in the temperature profiles.

In an embodiment of the method, the characteristics can include data indicative of a prediction of sodium/calcium exchanger behavior as an additional source of calcium at the presynaptic cradle as a function of an induced temperature included in the temperature profiles.

In an embodiment, a method of noninvasively treating a neurodegenerative disorder, can involve: modeling characteristics indicative of physical attributes of a central nervous system, the characteristics including parameters for diminishing adverse impacts of a magnetothermal stimulation treatment for a neurodegenerative disorder with respect to the central nervous system. Such a method can further involve applying as a part of the magnetothermal stimulation treatment and based on the characteristics of the physical attributes of the central nervous system, a magnetic field to the brain for a thermal stimulation of neuron cells within the brain.

In an embodiment, a system for noninvasively treating a neurodegenerative disorder, can include a magnetothermal stimulation device that applies as a part of a magnetothermal stimulation treatment for a neurodegenerative disorder with respect to the central nervous system and based on characteristics of physical attributes of the central nervous system, a magnetic field to the brain for a thermal stimulation of neuron cells within the brain.

In an embodiment of the system, the characteristics of the physical attributes of the central nervous system can include parameters for diminishing adverse impacts of the magnetothermal stimulation treatment for the neurodegenerative disorder with respect to the central nervous system.

In an embodiment of the system, the characteristics indicative of the physical attributes can include blood flow dynamics.

In an embodiment of the system, the characteristics indicative of the physical attributes can include magnetic nanoparticle interactions with blood capillary flow.

In an embodiment of the system, the characteristics indicative of the physical attributes can include heat transfer across at least one area of the brain.

In an embodiment of the system, the characteristics indicative of the physical attributes can include regulated neural signaling.

In an embodiment of the system, the characteristics indicative of the physical attributes can include one or more of: blood flow dynamics, magnetic nanoparticle interactions with capillary flow, heat transfer, and regulated neural signaling.

An embodiment of the system can further include an injection device for injecting nanoparticles into brain capillaries of the brain, wherein the nanoparticles are injected into the brain capillaries by the injection device prior to applying the magnetic field to the brain.

In an embodiment of the system, the characteristics indicative of the physical attributes can include temperature profiles within the central nervous system when exposed to the magnetic field.

In an embodiment of the system, the characteristics indicative of the physical attributes can include a brain tissue temperature distribution associated with the brain based on a finite element method.

In an embodiment of the system, the characteristics of the physical attributes can account for a movement of ions between presynaptic cradle and astrocyte soma under an influence of a temperature elevation included in the temperature profiles.

In an embodiment of the system, the characteristics can include data indicative of a prediction of sodium/calcium exchanger behavior as an additional source of calcium at the presynaptic cradle as a function of an induced temperature included in the temperature profiles.

In an embodiment, a system for noninvasively treating a neurodegenerative disorder, can include at least one processor and a memory, the memory storing instructions to cause the at least one processor to perform: determining characteristics indicative of physical attributes of a central nervous system, the characteristics including parameters for diminishing adverse impacts of a magnetothermal stimulation treatment for a neurodegenerative disorder with respect to the central nervous system; and applying as a part of the magnetothermal stimulation treatment and based on the characteristics of the physical attributes of the central nervous system, a magnetic field to the brain for a thermal stimulation of neuron cells within the brain.

In an embodiment, the instructions can be further configured to calculate a brain tissue temperature distribution associated with the brain based on a finite element method.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
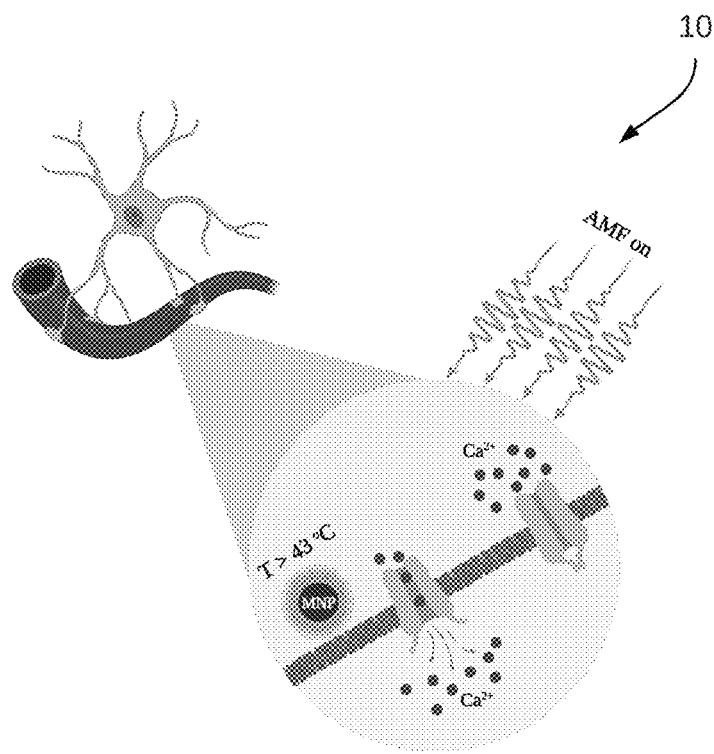
FIG. 1 illustrates a schematic diagram depicting magnetothermal DBS of heat sensitive ion channels (TRPV1$^+$) via MNPs as transducers, in accordance with an embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein do not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part. In addition, identical reference numerals utilized herein with respect to the drawings can refer to identical or similar parts or components.

In general, terminology may be understood, at least in part, from usage in context. For example, terms such as "and," "or," or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as "a," "an," or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Neurodegenerative disorders (e.g., Alzheimer's disease, Parkinson's disease, etc.) are signal irregularities in neuron cells. Deep brain stimulation (DBS) is a method for Parkinson's treatment. This method can manage Parkinson's symptoms, (e.g., tremor) by surgically implanting an electrode to deliver constant stimulation in deep brain levels. The fatal impact of DBS, however, has motivated scientists to propose a minimally invasive treatment, known as "Magnetothermal Neuromodulation". This technique can employ an alternating magnetic field (AMF) to excite injected transducers, e.g., magnetic nanoparticles (MNP). The magnetic nanoparticles exposed to the magnetic field can dissipate heat via thermal hysteresis. (Note that as utilized herein the term 'nanoparticles' can refer to 'magnetic nanoparticles' examples of which are transducers such as nanotransducers) The local elevated temperature can activate a type of heat-sensitive ion-channel, which can lead to a calcium cation ($Ca^{2+}$) influx. The $Ca^{2+}$ influx can eventually ameliorate the symptoms.

In the magnetothermal modulation, a primary aim is to reach a minimum temperature required for stimulation (e.g., 43° C.) and maintain the tissue temperature below 50° C. to avoid the thermal cytotoxic impacts. Hence, neurosurgical operations may seek thermo engineering theories to alleviate the risk levels and effectively administer remote therapies. The success and safety of the treatment may strongly rely on thermal interactions of the brain capillary wall with blood flow carrying heat dissipative nano-transducers.

The embodiments disclosed herein utilize microscale modeling of nanoparticles subject to magnetothermal stimulation and the consequences on the targeted neural circuits. As such, for medical advancements, the embodiments can provide a mathematical model that can extensively elaborate the physical attributes such as the blood flow dynamics, nanoparticle interactions with capillary flow, heat transfer, and the subsequent regulated neural signaling.

As discussed previously, thermal stimulation can employ a magnetic field (e.g., AMF, variable magnetic field, etc.) to excite magnetic nanoparticles (MNP) of which they are directly injected to the midbrain. The nanoparticles exposed to the magnetic field can dissipate heat via thermal stimulation (hysteresis). The local elevated temperature can activate a type of heat-sensitive ion-channel known as TRPV1, which leads to calcium cation influx. The calcium cation influx can eventually propagate signals in neurons, which can activate neuronal networks and ameliorates the Parkinson's symptoms. In the magnetothermal neuromodulation, the primary aim is to reach the minimum temperature required for stimulation which is 43° C. and maintain the tissue temperature below 50° C. to avoid thermal cytotoxic impacts.

In preliminary studies, thermal aspects of the aforementioned stimulation have been modeled. First, key parameters affecting the induced heating can be identified. Then, by using an optimization method and a damage analysis method for living tissues, a main goal was to optimize stimulation condition by which the temperature requirement for stimulation (43° C.) is satisfied with the least thermal damage.

As discussed previously herein, a technique to deliver magnetic nanoparticles to midbrain can involve direct injection, which is a technique that is slightly invasive. In accordance with the embodiments, however, promising progress in the drug delivery field can be implemented, which can take advantage of the fractal hierarchy of brain blood vessels by delivering the particles to the targeted midbrain through blood capillaries. An injection device such as the injection device 324 shown in FIG. 12 can be used to deliver the nanoparticles to the targeted midbrain through the blood capillaries. Such an injection however, would be preferably indirect, as discussed below.

The embodiments are based at least in part by a hypothesis by the inventors that the thermal stimulation from the particles inside the capillaries can effectively serve as a good alternative to a direct injection. To address this hypothesis: (i) we can establish a numerical package that accounts for the nano-transducer and blood flow interactions, and by considering the thermal and hydrodynamic aspects of the problem, we can effectively predict the temperature across the tissue. Furthermore, we will study the conditions that provide the stimulation requirement with negligible thermal cytotoxicity. We can also address the aforementioned hypothesis by (ii) then performing animal tests to verify the numerical model.

A current view in neuromodulation techniques implies that the presence of nanoparticles in the extracellular space (ECS), are capable of inducing calcium cation fluctuations. Moreover, experimental results indicate that the MNPs remained intact in the region that might cause major issues. This disclosure expresses a hypothesis proposal to eliminate the invasive injection and by aiming intravascular space, we can increase the tissue temperature. Therefore, first, we can determine whether this technique leads to the generation of action potential and calcium influx using slice electrophysiology and calcium imaging. Then, the stimulation requirements and restrictions corresponding to the proposed technique can be reconsidered and identified. A verified computational model can assist in evaluating the fraction of damage throughout the tissue.

Our results lead us to investigate the hypothetical impacts of the thermal stimulation on neural activities using brain slice calcium imaging and in vivo (live) calcium imaging which eventually lead us to establish a multi-compartmental mathematical model that accounts for the movement of ions between presynaptic cradle and astrocyte soma under influence of temperature variation. The model can predict the Sodium/Calcium exchanger (NCX) behavior as an additional source of calcium at the presynaptic cradle as a function of induced temperature.

| NOMENCLATURE | |
| --- | --- |
| Abbreviations | |
| AMF | Alternating Magnetic Field |
| CEM | Cumulative Equivalent Minutes |
| CNS | Central Nervous System |
| DBS | Deep brain stimulation |
| FD | Fractional Denaturation |
| FEM | Finite Element Method |
| LTNE | Local Thermal Non-Equilibrium |
| MAPE | Mean Absolute Percentage Error |
| MNP | Magnetic Nano Particle |
| OF | Objective Function |
| PD | Parkinson's Disease |
| SAR | Specific Absorption Rate |
| SLP | Specific Loss Power |
| TRPV | Transient Receptor Potential Vanilloid |
| VTA | Ventral Tegmental Area |
| Dimensionless numbers | |
| Le | Lewis Number |
| Re | Reynolds Number |
| St | Stokes Number |
| Latin symbols | |
| A | Frequency factor [1/s] |
| B | Rate of temperature change [° C./s] |
| $C_{MNP}$ | Concentration of MNP in aqueous solution [mg/mL] |
| $C_P$ | Specific heat [J/(kg° C.)] |
| $C_{Pb}$ | Blood specific heat [J/(kg° C.)] |
| D | Mass diffusion [m$^2$/s] |
| $d_p$ | Particle diameter [m] |
| $E_a$ | Activation energy [kJ/mol] |
| f | Frequency [1/s] |
| $H_o$ | Electromagnetic amplitude [A/m] |
| k | Thermal conductivity [W/(m° C.)] |
| $k_B$ | Boltzmann constant [(m$^2$ · kg)/(s$^2$ · K)] |
| $Q_m$ | Metabolic heat generation [W/m$^3$] |
| $Q_{source}$ | Heat source [W/m$^3$] |
| R | Universal gas constant [kJ/(mol° C.)] |
| r | Radius [cm] |
| $r_p$ | Particle radius [nm] |
| T | Temperature [° C.] |
| $T_b$ | Arterial blood temperature [° C.] |
| t | Time [s] |
| Greek symbols | |
| α | Thermal diffusivity [m$^2$/s] |
| β | Temperature factor |
| θ | Temperature dependent rate [° C./s] |

-continued

NOMENCLATURE

| | |
|---|---|
| μ | Dynamic viscosity [Pa · s] |
| ρ | Density [kg/m³] |
| $\rho_p$ | Particle density [kg/m³] |
| τ | Relaxation time [s] |
| $\omega_b$ | Blood perfusion [1/s] |

The direct and indirect financial burden of neurodegenerative diseases has become a significant issue in recent years. Particularly, in the United States, Parkinson's disease is known as the second-most common neurodegenerative disorder after Alzheimer's disease. In 2010, Parkinson's patients, approximately 630,000 people, incurred treatment expenses on the order of $14.4 billion. Costs are anticipated to increase due to the expected doubling in the elderly population by 2040. The crisis affecting Parkinson's patients motivated the present inventors to improve a potential thermal therapy to PD. In this disclosure, we attempt to establish optimal conditions for the therapy with effective as well as less destructive impacts on living tissues using a comprehensive modeling and simulation.

Parkinson's disease (PD) is a pathological condition, which is caused by the malfunction of the neuron cells in calcium cation regulation. Such a lack of $Ca^{2+}$ regulation can be specified by the aggregation of the protein, α-synuclein, which can ultimately lead to cell death. Profound understanding of corresponding factors in $Ca^{2+}$ signaling and associated contributions to PD progression are crucial to combat neurological implications. Such an understanding can enable us to achieve effective therapeutic approaches.

Deep brain stimulation (DBS) is a neurosurgical procedure and an established treatment that can ameliorate neurodegenerative symptoms. Currently, associated symptoms of PD can be treated by an approved, though invasive, therapy using permanently implanted electrodes. Serious drawbacks reported for this DBS technique have included: (1) permanent electrodes in the brain which can increase the risk of bleeding and infection, (2) invasive procedure of implantation, and (3) limited penetration depth.

To achieve a minimally invasive and remote neural excitation, scientists are highly motivated to propose new techniques. Regarding ineffectiveness and side effects of conventional stimulation; several other approaches have been developed in biomedical research centers in which stimuli technologies rely on acoustic, electromagnetic, or optical signals. Unlike other procedures, AMF enables signal delivery into certain deep regions within the brain. For PD, this technique can be implemented to target the ventral tegmental area (VTA), without causing any significant lesions.

Magnetic transducers (e.g., magnetic nanoparticle (MNP)), in conjunction to magnetic neuromodulation can impose heat or a force on CNS. In magnetothermal excitation, nanoparticles can convert magnetic field energy to heat via thermal hysteresis. The heat ultimately can activate heat-sensitive ion channels (e.g., transient receptor potential vanilloid (TRPV)), responsible for $Ca^{2+}$ exchange. Studies on rodents have shown that the injected iron-based MNPs coated with biocompatible materials insure their solubility in aqueous physiological solutions, which may minimize the risk of coagulation. In particular, iron oxide ($Fe_3O_4$) as a nanoparticle has a great potential for neuromodulation, since it can get recycled through the metabolic pathways.

It has been shown that 22 nm spherical $Fe_3O_4$ particles, for example, when exposed to AMF have the highest specific loss power (SLP). According to experimental investigations, MNPs injected to the VTA seem to disperse within at most two months after injection with minimal uptake. This may indicate that magnetothermal stimulation can be an entirely safe procedure for treatment of neuropsychiatric/neurodegenerative disorders such as Alzheimer's disease and Parkinson's disease.

In experiments, generated heat evoked channel openings have been used at 44° C. In other investigations, the induced temperature increase in excess of 43° C. has exhibited changes in intercellular $Ca^{2+}$ concentration. A computational model has indicated that the minimum temperatures for hyperthermia treatment and thermal ablation are 42° C. and 50° C., respectively. Other techniques claim that thermotherapy using MNPs was well tolerated by patients with temperatures ranging from 42.4° C. to 49.5° C. To accomplish safe hyperthermic treatments, however, it may be required to reach a minimum temperature requirement for stimulation. Meanwhile, it is vital to avoid marginal temperatures that can lead to cell death.

In order to induce selective and controllable heating in the brain tissue, first, the product of electromagnetic frequency and amplitude ($f \times H_o$) must be restricted to be less than $5 \times 10^9$ [A/(m·s)]. Second, MNP aqueous solutions can be required to be administered at low concentrations. Ultimately, by applying these conditions, it is expected that TRPV channels can be engineered for the purpose of neural $Ca^{2+}$ influx regulation.

Some computational models have been widely used to model and simulate biological material under hyperthermic procedure. The computational models have been validated with available experimental studies and can be applied to predict thermal response of brain tissue to magnetic neuromodulation. These attempts take into account (1) conduction through the tissue (2) convection heat transfer inside the tissue due to blood flow and (3) metabolic heat generation.

In 1948, Pennes proposed a simplified version of the energy equation that accounts for blood perfusion and metabolic heat generation. Others have investigated thermal therapy potentials of electromagnetic radiation by means of a finite element method. Still others have studied heat transfer behavior of blood and tissue for various biological media during the ablation process. Furthermore, a theoretical approach has been developed for temperature changes in the brain depending on physiological boundaries that shows the impacts of blood flow on the regional temperature. An LTNE method has been developed to model bioheat transport through biological medium subjected to an electromagnetic field with a specific absorption rate (SAR).

In an embodiment, aspects of a newly established DBS procedure based on imposing a magnetic field can be modeled and computationally simulated. Yet, at present, lack of quantitative understanding of thermal behavior in such DBS treatments has been shown to limit an effective stimulation. A main goal of the embodiments is to improve the efficacy of wireless magnetothermal stimulation by obtaining the optimized conditions for neural activation. For this purpose, it is crucial to provide a uniform temperature across the tissue. Meanwhile, it is essential to maintain the raised temperature within the benign domain. To identify influential parameters, the lesion size that the brain tissue endures after exposure can be evaluated. Numerous modes of biomaterial damage are known to occur in the targeted brain tissue due to hyperthermic treatments; as such, here we restrict our attention only to cytotoxic damage vis-a-vis irreversible protein denaturation. Ultimately, for the first time, we employ a free-derivative optimization method to provide the optimum quantitative variables, namely: MNP concentration, volume of MNP solution and exposure time.

In an embodiment, magnetic fields (e.g., low frequency alternating magnetic fields) can penetrate deep into the brain regions with low attenuation and subsequently be absorbed by superparamagnetic nanoparticles. This implies that MNP solutions exposed to AMF, can dissipate heat via hysteretic power loss. Temperature rise of the targeted VTA demonstrates a significant TRPV1$^+$ trigger and sporadic activation in TRPV1$^-$. Subsequently, an increase in calcium cation (Ca$^{2+}$) influx can be observed. For example, FIG. 1 illustrates a schematic diagram 10 depicting magnetothermal DBS of heat sensitive ion channels (TRPV1$^+$) via MNPs as transducers, in accordance with an embodiment.

Based on earlier works and evaluation of a group of pertinent dimensionless numbers, the mass diffusion can be neglected within the short time span, which may be characteristic of magnetic stimulation. The physical paradigm of brain tissue and the governing equations are discussed in detail. To acquire an accurate prediction of the damaged tissue, two methods may be employed. One method can provide an overestimation, while the other method involves an underestimation over lesion size. Further, the grid independence test and the numerical specifications including time and grid sizes are presented in detail. In an optimization section herein, the objective function and the constraint considered for the free derivative based optimization, are elaborated.

In an embodiment, we can make use of Pennes' equation in simulation and optimizations. Before using Pennes' equation, however, we can evaluate that we are in the appropriate regime for its use. We can establish that the diffusion of MNP can be negligible for short time spans. To accomplish this goal: we can show that the Lewis number is significantly larger than unity, which can imply the negligibility of mass diffusion compared to thermal diffusion.

Since the Reynolds number for this application is very small compared to unity (Re=$\rho u d / \mu \approx 0.11 \ll 1$), the dynamical regime is within the Stokes flow regime. The other dimensionless number, Stokes number, corresponds to the behavior of suspended particles. Stokes number specifies the dominance of particle's inertia in the flow. Fluid flows with small Stokes numbers unveil that particles follow the flow streamlines. Low Stokes number demonstrates the validity of mass transfer equation for MNPs.

$$St = \frac{\tau u}{d} = 3.42 \times 10^{-12} \ll 1 \quad (1)$$

$$\tau = \frac{\rho_p d_p^2}{18\mu} \quad (2)$$

There are two types of mass diffusion within the brain tissue: Brownian motion diffusion and particle scattering due to capillaries. Brownian accounts for random motions of particles owing to thermal variations.

$$D_{Brownian} = \frac{k_B T}{6\pi \mu r_p} = 3.9 \times 10^{-12} m^2/s \quad (3)$$

The diffusion under influence of blood cells is in the order of $D_{Scattering}=10^{-11}$-$10^{-10}$ m$^2$/s. Therefore, the total particle diffusion is the sum of Brownian and scattering diffusions ($D_{total}=D_{Scattering}+D_{Brownian}\approx 10^{-10}$). Eventually, by calculating the Lewis number, it can be realized that mass diffusivity is negligible in a short period of stimulation (e.g., 10 minutes). In the literature, experimental results confirm that MNPs have remained intact in the targeted region for a couple of weeks after injection.

$$Le = \frac{\alpha}{D} = 1.36 \times 10^3 \gg 1 \quad (4)$$

Heat transfer through biomaterials is a combination of several mechanisms including conduction, convection via blood perfusion and heat generation due to metabolic activities. There are many numerical models available in the literature to take into account these biological mechanisms, which are in compliance with clinical experiments. In most recent medical endeavors made for development of new minimally invasive techniques for PD treatment, Pennes' equation was used for ease of computations as well as high accuracy. Regarding the above justifications for mass diffusion negligibility, Pennes' equation can be used. To predict the temperature response to AMF, a finite element method (FEM) can be utilized. Heat transfer inside the brain tissue can be modeled by means of transient bioheat equation given as:

$$\rho C_P \frac{\partial T}{\partial t} = k \nabla^2 T - \omega_b \rho_b C_{Pb}(T - T_b) + Q_m + Q_{source} \quad (5)$$

where t [s] is the time, $Q_{source}$ [W/m$^3$] the heat source generated by MNPs exposed to AMF. $\rho$ [Kg/m$^3$] the tissue density, $C_P$ [J/(Kg° C.)] the tissue specific heat, k [W/(m° C.)] conductivity of the tissue, $\omega_b$ [1/s] representing the blood perfusion rate, $\rho_b$ [Kg/m$^3$] the blood density, $C_{Pb}$ [J/(Kg° C.)] the blood specific heat, $T_b$ [° C.] the arterial blood temperature and $Q_m$ [W/m$^3$] is the spatially uniform metabolic heat generation.

Figure 2:
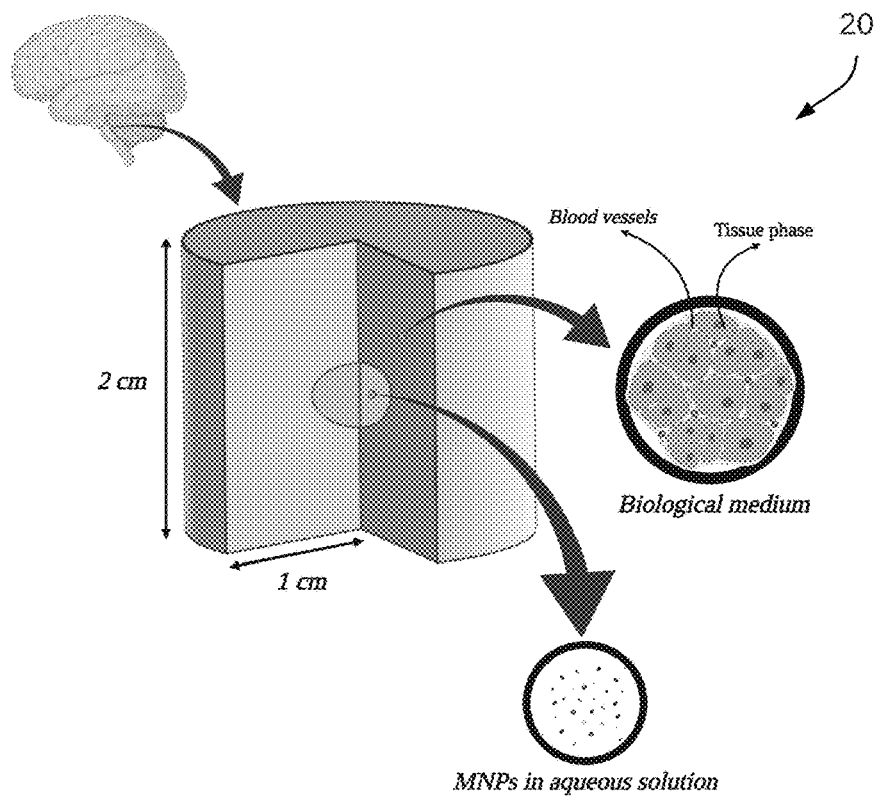
FIG. 2 illustrates a schematic diagram of brain tissue injected with MNP solution, in accordance with an embodiment.

FIG. 2 illustrates a schematic diagram 20 of brain tissue injected with MNP solution, in accordance with an embodiment. In an experimental embodiment, a 2.5 μL injection of MNP solution with 100, 50 and 10 mg/mL of concentration can be considered at the center of cylindrical biomaterial with brain tissue properties as shown in FIG. 2. The brain tissue and blood flow properties as well as imposed magnetic heat source magnitudes are provided in Table 1. The volumetric heat generation denoted by $Q_{source}$ in Equation 5 is the product of SLP (700 W/g). The concentration of 22 nm Fe$_3$O$_4$ MNP solution ($Q_{source}$=SLP×c$_{MNP}$) as the corresponding values are listed in Table 1 below.

TABLE 1

| Thermophysical properties | | |
|---|---|---|
| Material | Parameter | Value |
| Brain | Density of tissue [Kg/m$^3$] | 1065 |
|  | Specific heat of tissue [J/(kg° C.)] | 3630 |
|  | Thermal conductivity [W/(m° C.)] | 0.51 |
|  | Metabolic heat generation [W/mL] | 0.025 |
| Blood | Arterial blood temperature [° C.] | 37 |
|  | Density of the blood [kg/m$^3$] | 1050 |
|  | Blood specific heat [J/(kg° C.)] | 3617 |
|  | Blood perfusion rate [1/s] | 0.004 |
|  | Blood Viscosity [mPa · s] | 5.5 |
|  | Blood Thermal Conductivity [W/(m° C.)] | 0.52 |

TABLE 1-continued

Thermophysical properties

| Material | Parameter | Value |
|---|---|---|
| AMF | AMF volumetric heat generation for 100 mg/mL [W/mL] | 70 |
| | AMF volumetric heat generation for 50 mg/mL [W/mL] | 35 |
| | AMF volumetric heat generation for 10 mg/mL [W/mL] | 7 |

The initial temperature can be set to be equal to the normal body temperature (Eq. 6). Brain tissue material and MNP solution can be assumed to be uniform in terms of thermophysical properties. Tissue temperature and the solution temperature at the interface can be considered to be equal (Eq. 7). The outer surface temperature of cylinder can be assumed as constant temperature regarding the large scale of brain tissue containing aqueous solution (Eq. 8).

$$T_{initial} = 37° C. \quad (6)$$

$$T_{solution\ @\ interface} = T_{tissue\ @\ interface} \quad (7)$$

$$T_{@r=1\ cm} = 37° C. \quad (8)$$

Figure 3:
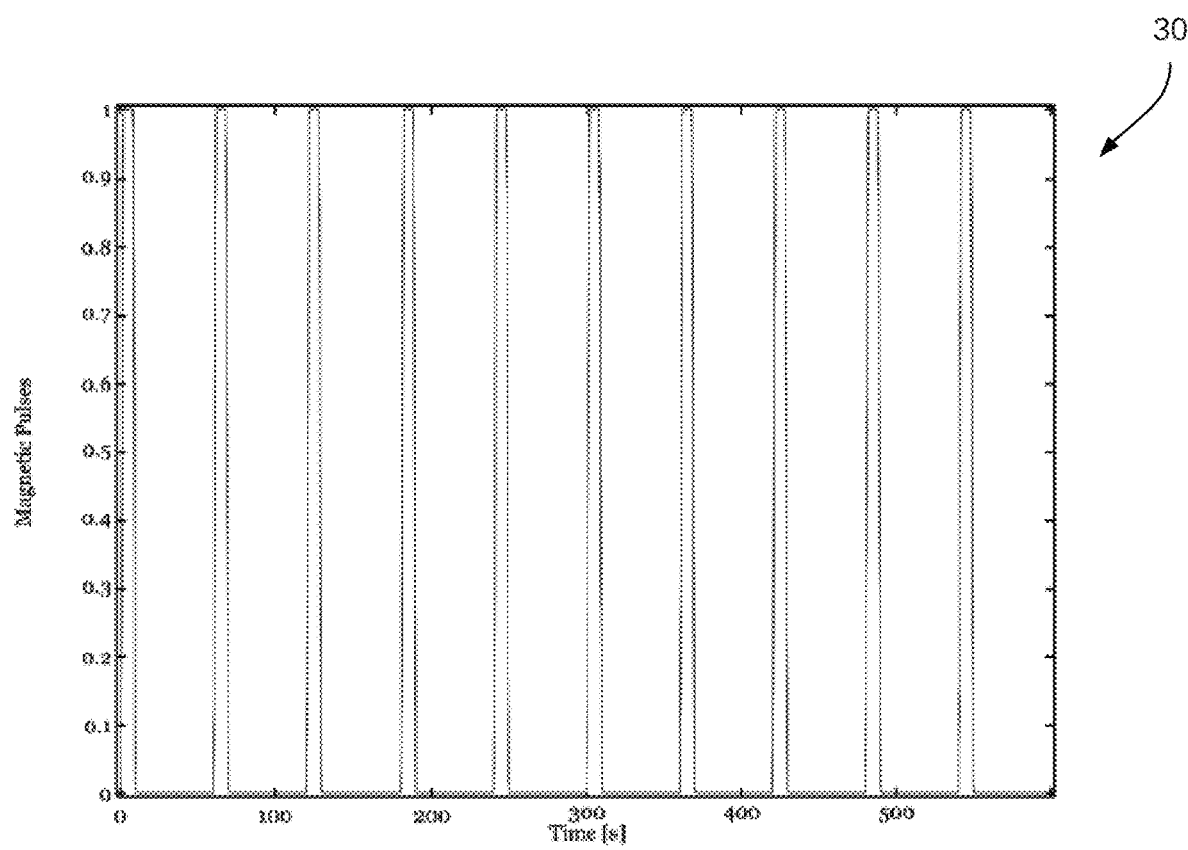
FIG. 3 illustrates a graph depicting data indicative of heat source pulses over a ten-minute stimulation period, in accordance with an embodiment.

To maintain tissue temperature within benign temperature domain, electromagnetic fields can be applied in, for example, ten-second stimulation pulses, which can enable a medium temperature to rise up to, for example, 43° C. Afterwards, during typical fifty-second rest, the tissue cools down back to the body temperature. This entire sixty-second epochs, which can be prolonged for 10 minutes of intermittent exposure, for example, can prevent thermal cytotoxic effects (see FIG. 3). FIG. 3 illustrates a graph 30 depicting data indicative of heat source pulses over a ten-minute stimulation period, in accordance with an embodiment.

A challenge in hyperthermia is to evaluate cell survival upon exposure to an elevated temperature. Experimental results show the exponential growth of cell injury in response to an exposure time. For magnetothermal stimulation, however, comprehensive information about tolerance of tissue to long-time-high temperature can be required. In a protein denaturation model termed as the Lumry-Eyring model, it can be assumed that protein denaturation happens in two steps: (1) reversible unfolding of native protein (N); and (2) irreversible change of unfolded protein (U) leading to the final denatured state (D).

$$N \leftrightarrows U \mapsto D \quad (9)$$

It has been reported that long-term exposure of tissues to heating conditions can result in protein denaturation, an irreversible form of cytotoxic cellular damage. In the embodiments, two mathematical models relating to protein denaturation, as a function of tissue temperature, can be considered. These models are the "Cumulative time method" and the "Arrhenius method"; these are presented below in Equation 10 and Equation 11, respectively.

For the cumulative time method (thermal dose), according to available investigations, cumulative equivalent minutes ($CEM_{43}$) can be defined as:

$$CEM_{43} = \int \beta^{43-T(t)} dt \quad (10)$$

where $\beta=0.5$ for temperatures higher than 43° C. and $\beta=0.25$ for temperatures below 43° C. and the cumulative equivalent minutes must not exceed the critical thermal threshold. Despite experiments conducted determining the thermal threshold for brain damage analysis, and in regard to the complexity to discriminate between an adverse impacts and normal physiological responses in brain, thermal thresholds reported in the literature demonstrate a great variability in sensitivity to dissipated heat ranging from 1 to 390 minutes. Hence, $CEM_{43}$ is not appropriate and accurate enough for damaged brain tissue predictions. To compare cumulative time method results with the Arrhenius method, a lesion size assessment can be carried out for HuH-7 cells with a thermal threshold of 340 minutes. To calculate the damage fraction, $CEM_{43}$ can be divided by thermal threshold.

The Arrhenius method is a prominent model, which has been extensively used for evaluating protein denaturation and cell injury. This method can demonstrate high compliance with empirical observations for various cell types. Thermotolerance of biomaterials can be examined via a first order irreversible rate process. The Arrhenius method for lesion size prediction through the tissue is described by equations (11) and (12) given below:

$$FD(T) = 1 - \exp\left[-\frac{1}{B}\int_{T_0}^{T_{end}} \theta dT\right] \quad (11)$$

$$\theta = A\exp\left(-\frac{E_a}{RT}\right) \quad (12)$$

where FD(T) is the targeted tissue fractional as a function of temperature, B is rate of temperature change, and θ is temperature dependent rate. $E_a$ and A are the activation energy and frequency factor, respectively. Depending on the protein types, the activation energy can vary between, for example, 100 to 800 [kJ/mol] and the frequency factor can vary between $10^9$ and $10^{129}$ [1/s]. To compare this model with $CEM_{43}$, kinetic parameters for HuH-7 cells can be chosen based on the values listed in Table 4, and with $E_a=323.8$ [kJ/mol] and $A=5.316\times10^{50}$ [1/s]. Furthermore, for damage analyses and the optimizations, activation energy and frequency factor for the brain tissue, can be selected based on a highly consistent model to be 628 [kJ/mol] and $3.1\times10^{98}$ [1/s], respectively.

Medical results demonstrate that cumulative time method tends to overestimate the lesion size. While, the associated calculations for Arrhenius method show an underestimation of lesion size against the corresponding cell injury according to empirical observations. Essentially, it is required to carefully examine the cytotoxic effects for both approaches.

Figure 4:
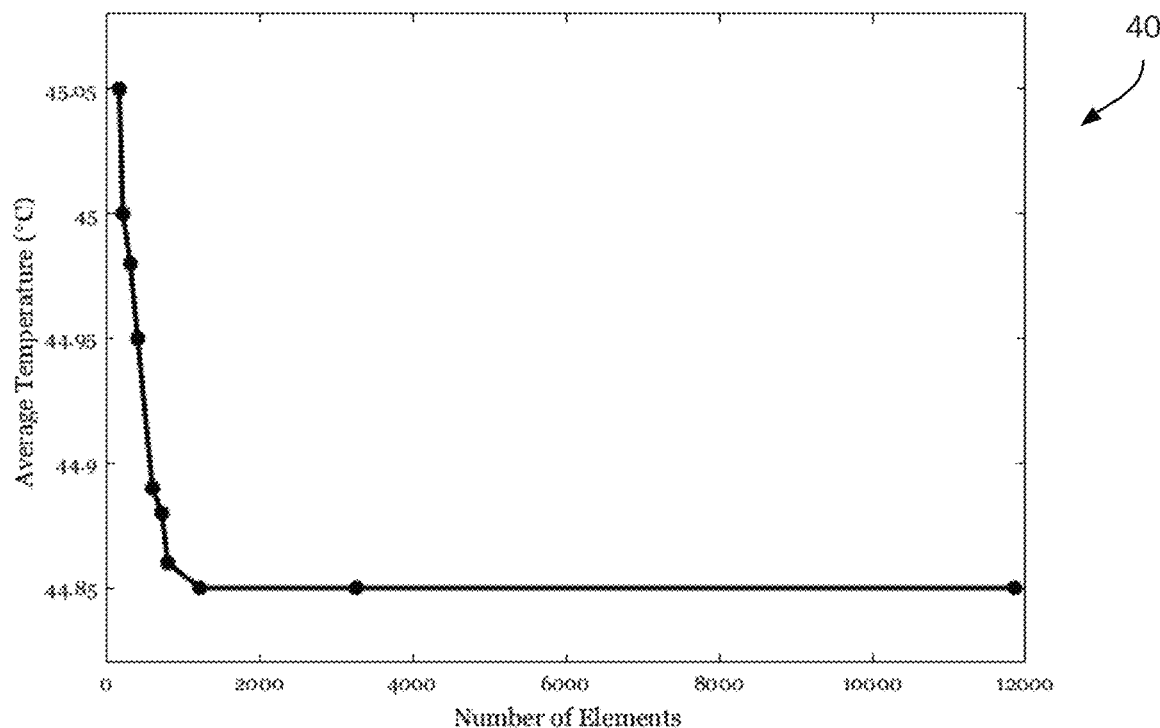
FIG. 4 illustrates a graph depicting grid independent analysis of a computational model, in accordance with an embodiment.

In some embodiments, a numerical solution procedure can be implemented. For example, a finite element method can be utilized to discretize Pennes' equation (Eq. 5). A structured numerical mesh composed of triangular elements can be used to discretize the computational model. The convergence criterion can be set to monitor the reduction of the residuals to $10^{-6}$. In a transient heat transfer analysis with second-order elements, there can be a relationship between minimum time step and element size.

$$\Delta t > \frac{\rho C_P}{6k}\Delta l^2 \quad (13)$$

where Δt is time step and Δl refers to element size. To capture the induced magnetic pulses, it may be required to have a small time increment, which can be subsequently assigned to be 0.01 s. On the other hand, according to Eq. 13, the element size must be less than 0.089 mm. Adequate sensitivity analyses have been applied to demonstrate the independence of the computational results from the mesh resolution. The average temperature variation of biological tissue at the end of the last pulse versus the number of elements is depicted FIG. 4. The independence of numerical results from the mesh size can be established around 1300 elements. It demonstrates that the maximum element size of 0.07 mm is sufficiently fine to provide accurate results. FIG. 4 illustrates a graph 40 depicting grid independent analysis of a computational model, in accordance with an embodiment.

For designing and optimizing the neuromodulation, it may be crucial to find the optimum parameters estimation. Decision variables including exposure time, concentration and volume of MNP solution can play a significant role in the temperature distribution. To achieve reasonable numbers for decision variables and to simplify the optimization approach, the variables are restricted by integer values. In order to only consider integer values, a derivative-free optimization method (Nelder-Mead Method) can be employed. The objective function can be assigned to minimize the average damage fraction based on Arrhenius method over a central 2 mm diameter sphere. Thus, the objective function can be derived by the integration of Eq. 11 over 2 mm sphere, yielding:

$$OF = \iiint_{2mm\,sphere} 1 - \exp\left[-\frac{1}{B}\int_{T_0}^{T_{end}} \theta dT\right] \quad (14)$$

To meet the excitation requirement, it is essential that the final average temperature reaches 43° C. Whereas, based on the work of Cervadoro et al., maintaining the tissue temperature below 50° C. may be crucial, due to low thermal tolerance reported for the brain. Thus, as a constraint to this optimization, the resulting temperature may be forced to be within the safe domain (e.g., 43° C.<$T_{tissue}$<50° C.).

Despite past attempts to increase the accuracy of computational models and although, previously proposed models are theoretically more accurate than the basic Pennes' equation. There still exists, however, technical obstacles like measuring some experimental parameters, which can create difficulty in employing these previously models. In using Pennes' bioheat equation, we are within its acceptable limitations such as neglecting the hydrodynamic impacts of blood flow on tissue, thermal equilibrium assumption in capillary scale and constant blood temperature.

Figure 5:
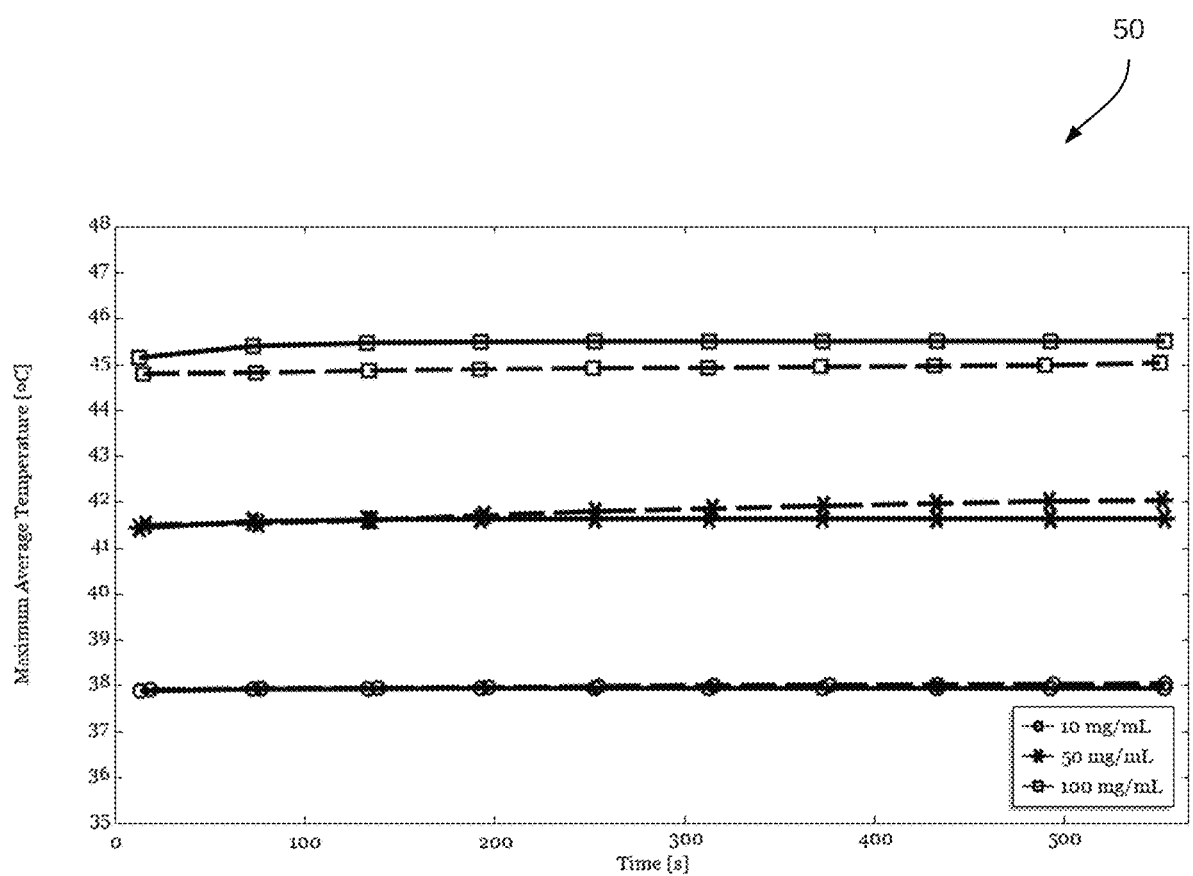
FIG. 5 illustrates a graph depicting data comparing the present numerical solution (solid lines) with an investigation (dashed lines) for various concentrations of MNP aqueous solution, in accordance with an embodiment.

The quantitative results acquired from the proposed model can be compared with experimental results provided by Chen et al. In this investigation, Chen et al demonstrated minimally invasive and remote neural excitation through the stimulation of TRPV1 ion channels by using magnetic nanoparticles. Their experiments relied on brain tissue exposure to heat excitation of MNPs with 100, 50 and 10 mg/mL of concentration. Ten-second pulses of AMF at 15 kA/m and 500 kHz with fifty-second rest intervals were delivered to the tissue over 10 minutes. The pulsating magnetic field provided 700 W/g of heat source within 2.5 μL of MNP solution. FIG. 5. shows the trend of maximum average temperatures at the end of 10-second induced magnetic pulses for various concentrations. That is, FIG. 5 illustrates a graph 50 depicting data comparing the present numerical solution (solid lines) with an investigation (dashed lines) for various concentrations of MNP aqueous solution, in accordance with an embodiment.

It can be observed that the proposed model in of the disclosed embodiments is in excellent agreement with the experimental results obtained by Chen et al. Standard deviation of our model from the experimental results presented by Chen et al. demonstrates the high accuracy of our model based on a mean absolute percentage error (MAPE). The calculated errors for 100, 50 and 10 mg/mL of MNP concentrations are, for example, 1.13%, 0.5% and 0.2%, respectively.

Figure 6A:
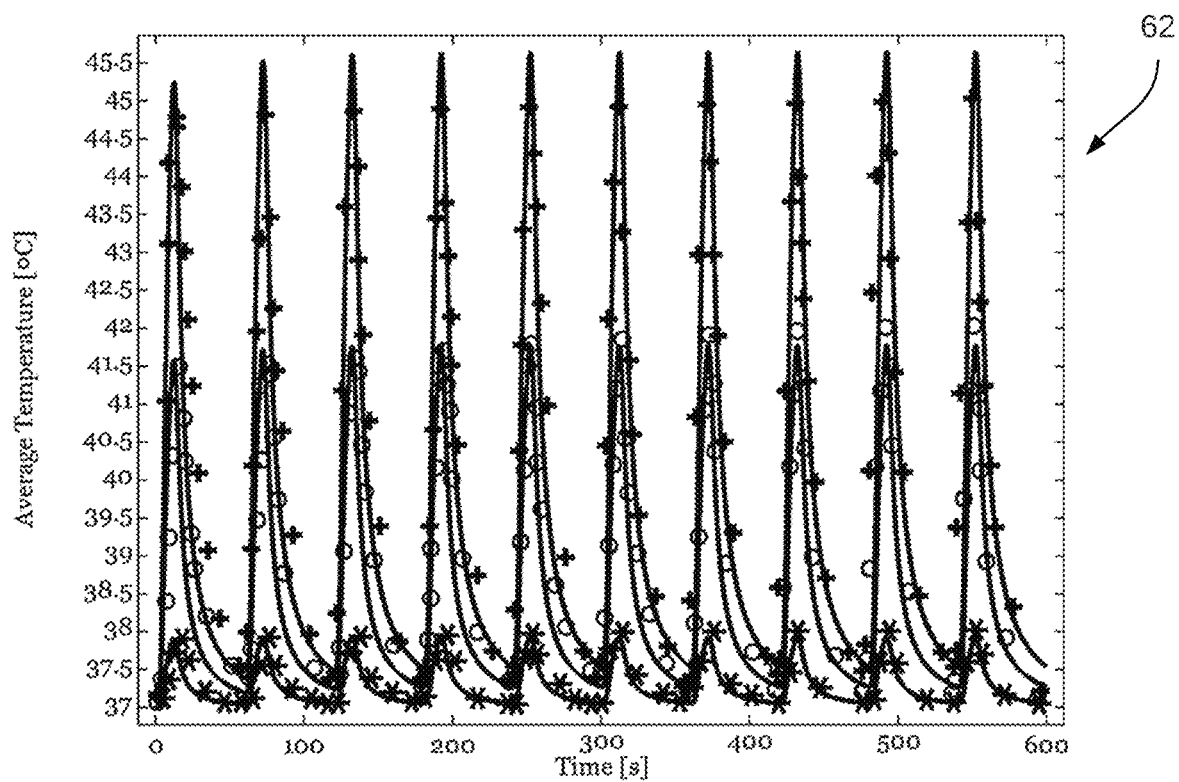
FIG. 6(a) illustrates a graph depicting data indicative of tissue average temperature over a ten minute magnetic field radiation based on numerical results (solid line) and experimental results (markers) for different concentrations, in accordance with an embodiment.

FIG. 6(a) illustrates a graph 62 depicting data indicative of tissue average temperature over a ten-minute magnetic field radiation based on numerical results (solid line) and experimental results (markers) for different concentrations, in accordance with an embodiment. To examine the impact of pulsating thermal activations, other computational simulations were carried out incorporating various imposed heat source values. Graph 62 of FIG. 6(a) depicts the resulting average temperature over a ten-minute exposure are in very good agreement with the empirical observations. The corresponding imposed heat source values that interact with concentrations of 100, 50 and 10 mg/mL are 70, 35 and 7 W/mL, respectively.

As expected, due to the pulsating heat source, the consequential temperature is intermittent in which the average temperature reaches the maximum value at the end of the ten-second pulses and cools down to the body temperature in the fifty-second rest time. It can be seen that higher concentrations of aqueous solution lead to higher values of heat source values exerted on the targeted region and subsequently, higher temperatures can be attainable. FIG. 5 and FIG. 6a show a gradual increase in temperature amplitude over the intervals. As can be seen, the peak temperature reaches 45.5° C., 42° C. and 38° C. for 100, 50 and 10 mg/mL concentrations at the end of the exposure time. Only a 100 mg/mL concentration meets the minimum temperature that can be required ($T_{tissue}$>43° C.) for TRPV1 activation.

Figure 6B:
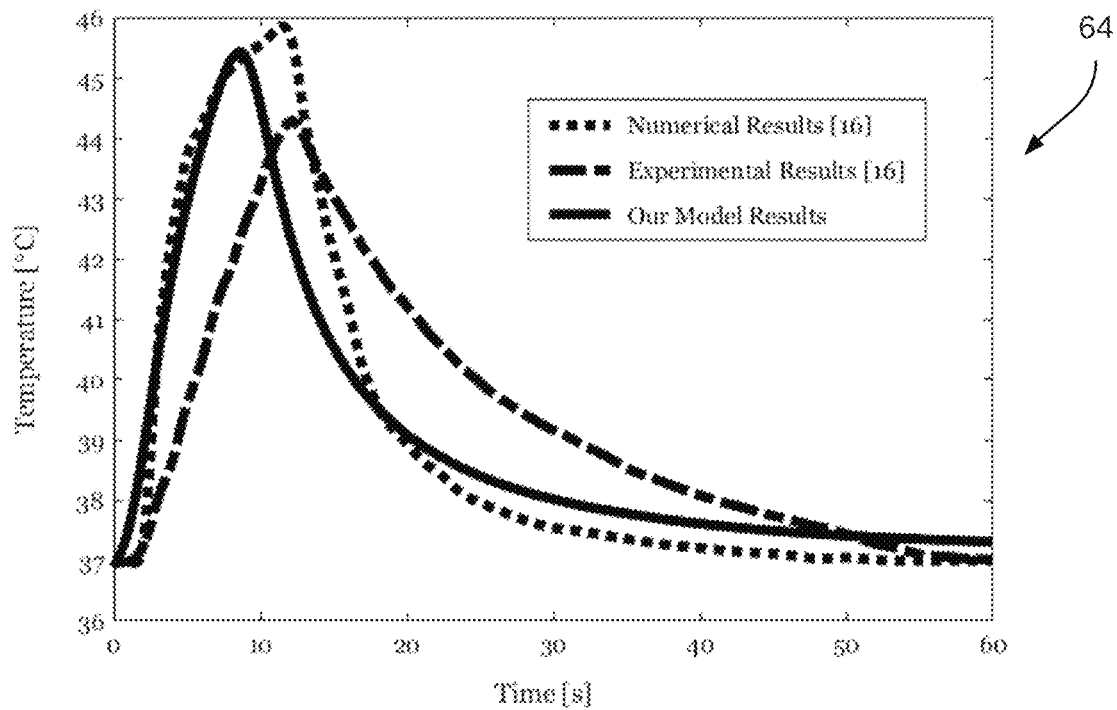
FIG. 6(b) illustrates a graph depicting data indicative of a comparison between a computational model and available numerical and experimental results for the first pulse with 100 mg/mL of MNP concentration, in accordance with an embodiment.

FIG. 6(b) illustrates a graph 64 depicting data indicative of a comparison between a computational model and available numerical and experimental results for the first pulse with 100 mg/mL of MNP concentration, in accordance with an embodiment. FIG. 6(b) illustrates the corresponding results of our model and an available experimental and numerical investigation with 100 mg/mL MNP concentration for the first pulse of magnetic field, which can represent the largest deviation compared to other concentrations (i.e., see FIG. 6(a)).

Figure 7A:
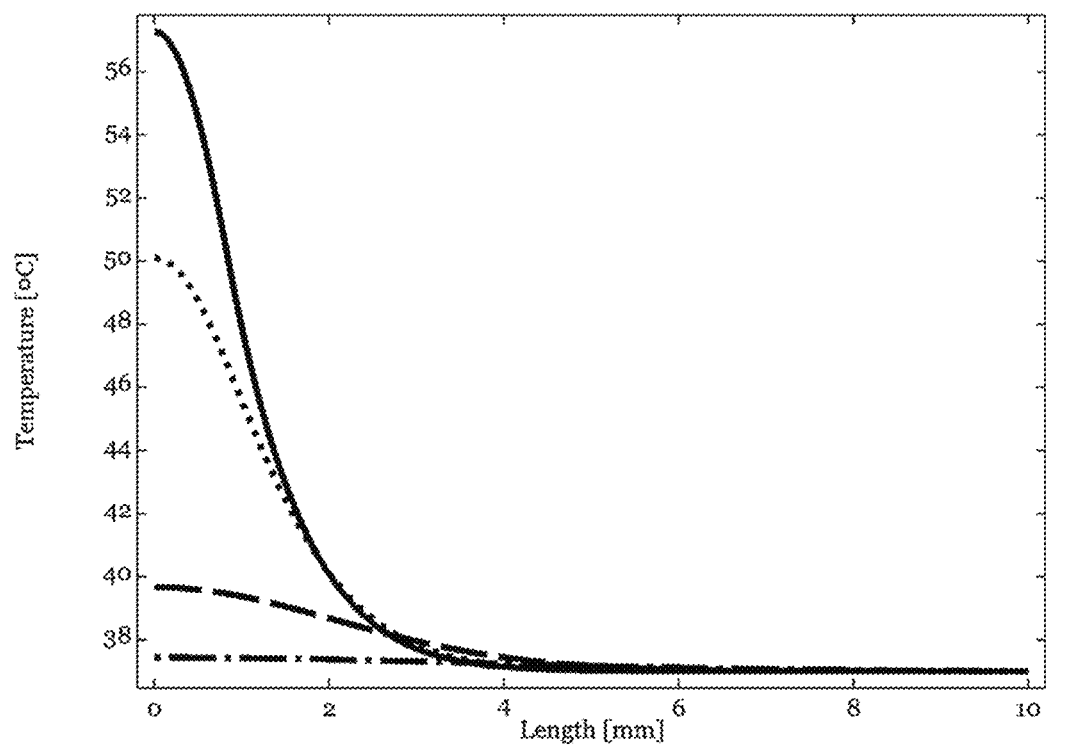
FIG. 7(a) illustrates a graph depicting data indicative of temperature variation along the radial length at different times for 100 mg/mL 10 second (solid line), 11 second (dotted line), 20 second (dashed line) and 60 second (dash-dot line), in accordance with an embodiment.

FIG. 7(a) illustrates a graph 72 depicting data indicative of temperature variation along the radial length at different times for 100 mg/mL 10 second (solid line), 11 second (dotted line), 20 second (dashed line) and 60 second (dash-dot line), in accordance with an embodiment. Graph 72 of FIG. 7(a) shows the local temperature along a line from the injected droplet center to the outer surface of the cylinder at different times. The results demonstrate substantial temperature variation along the radial length. At the end of the ten-second pulses, this figure indicates that at the center, the local temperature increases by 57° C. and then gradually decreases to 37° C. at the end of sixty-second cycle. All experimental studies have primarily mentioned the average temperature due to the measurement limits on the device, while the numerical results show that the local temperature at some points is elevated beyond an acceptable limit leading to the death of the cells in its close proximity. Crossing the benign temperature domain particularly at the center and in the vicinity of aqueous solution implies that it is crucial to employ damage analysis.

Figure 7B:
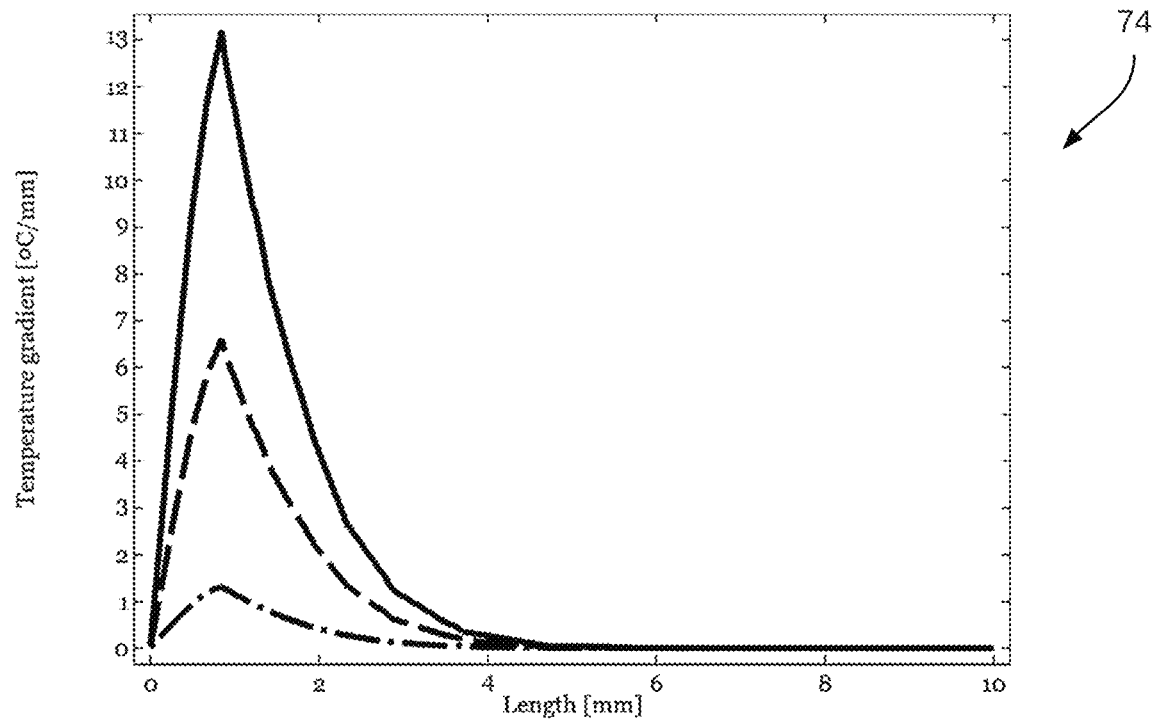
FIG. 7(b) illustrates a graph depicting data indicative of a temperature gradient along the radial length for different concentrations at t=10 s: 100 (solid line), 50 (dashed line) and 10 (dash-dot line) mg/mL, in accordance with an embodiment.

FIG. 7(b) illustrates a graph 74 depicting data indicative of a temperature gradient along the radial length for different concentrations at t=10 s: 100 (solid line), 50 (dashed line) and 10 (dash-dot line) mg/mL, in accordance with an embodiment. Graph 74 of FIG. 7(b) illustrates temperature gradient at the tenth second after exposure for different concentrations. It can be observed that for lower concentrations, the temperature distribution is more uniform. Realization of a uniform temperature distribution enables maintaining the tissue from local thermal damage caused by regional temperature spikes.

Figure 8A:
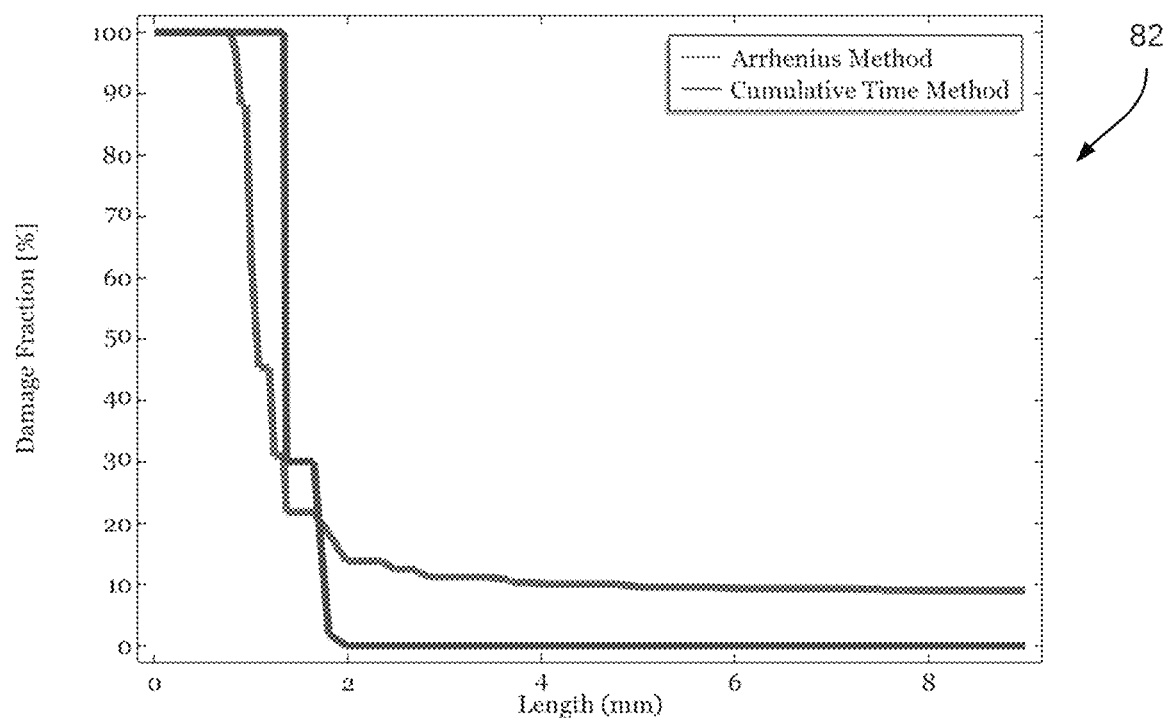
FIG. 8(a) illustrates a graph depicting data indicative of damage analysis for HuH-7 cells based on Arrhenius method and Cumulative Time method for 100 mg/mL of concentration, in accordance with an embodiment.

FIG. 8(a) illustrates a graph 82 depicting data indicative of damage analysis for HuH-7 cells based on Arrhenius method and Cumulative Time method for 100 mg/mL of concentration, in accordance with an embodiment. As mentioned earlier, cumulative time method leads to an overestimation of lesion size compared to Arrhenius method. Far away from the injected droplet as illustrated in graph 82 of FIG. 8(a), the damage for HuH-7 cells is low based on the two prominent methods. Towards the centerline the lesion size gets larger. Both methods demonstrate that in the neighborhood of 1 mm radius far from the center, the fraction of damage to the neurons is really high and it increases by 100% and 70%, respectively based on cumulative time method and Arrhenius method.

Figure 8B:
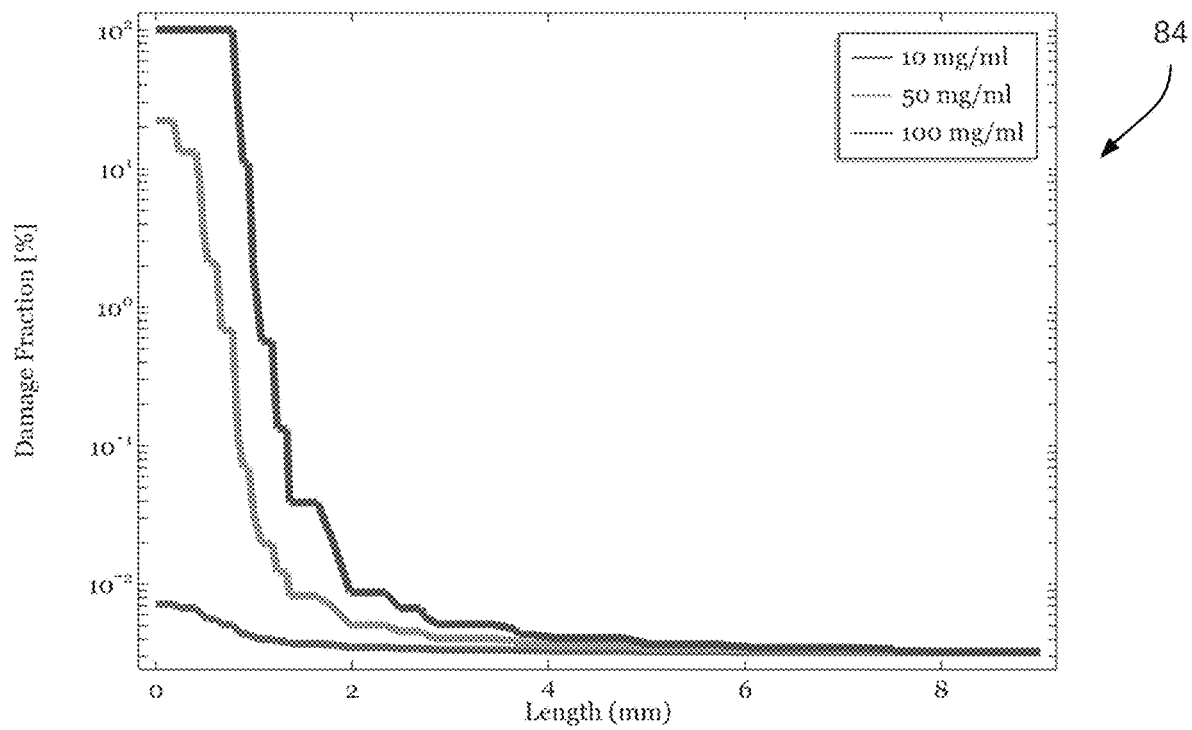
FIG. 8(b) illustrates a graph depicting data indicative of Arrhenius method results for targeted brain tissue with various concentrations of MNP solutions, in accordance with an embodiment.

FIG. 8(b) illustrates a graph 84 depicting data indicative of Arrhenius method results for targeted brain tissue with various concentrations of MNP solutions, in accordance with an embodiment. FIG. 8(b) depicts the fraction of the damaged brain tissue for 100, 50 and 10 mg/mL of concentration based on Arrhenius method. The average fraction of damage within a 1 mm radius neighborhood for 100, 50 and 10 mg/mL are 66.2%, 2.1% and 0.005%, respectively. Despite negligible fraction of damage for corresponding low concentrations, according to FIG. 6(a) and FIG. 6(b), not reaching the minimum temperature in 10-minute exposure time makes it an undesirable condition for the magnetic stimulation.

Figure 9A:
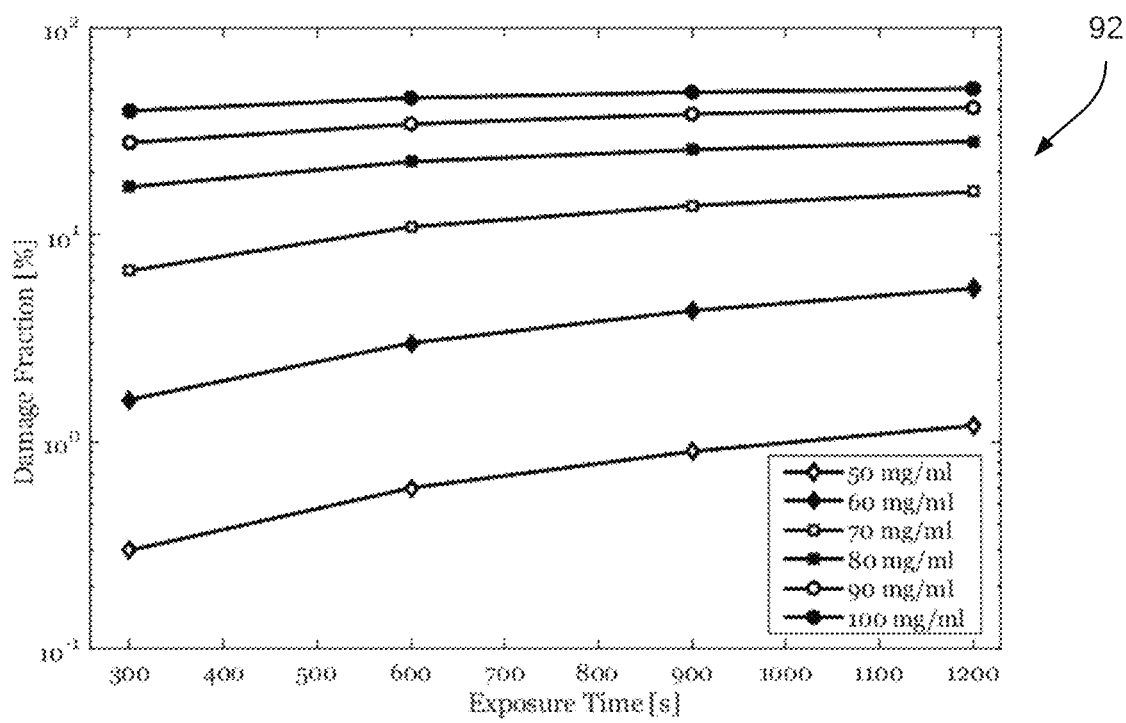
FIG. 9(a) illustrates a graph depicting data indicative of the impact of various exposure time on brain tissue for 2 mm$^3$ of solution, in accordance with an embodiment.
Figure 9B:
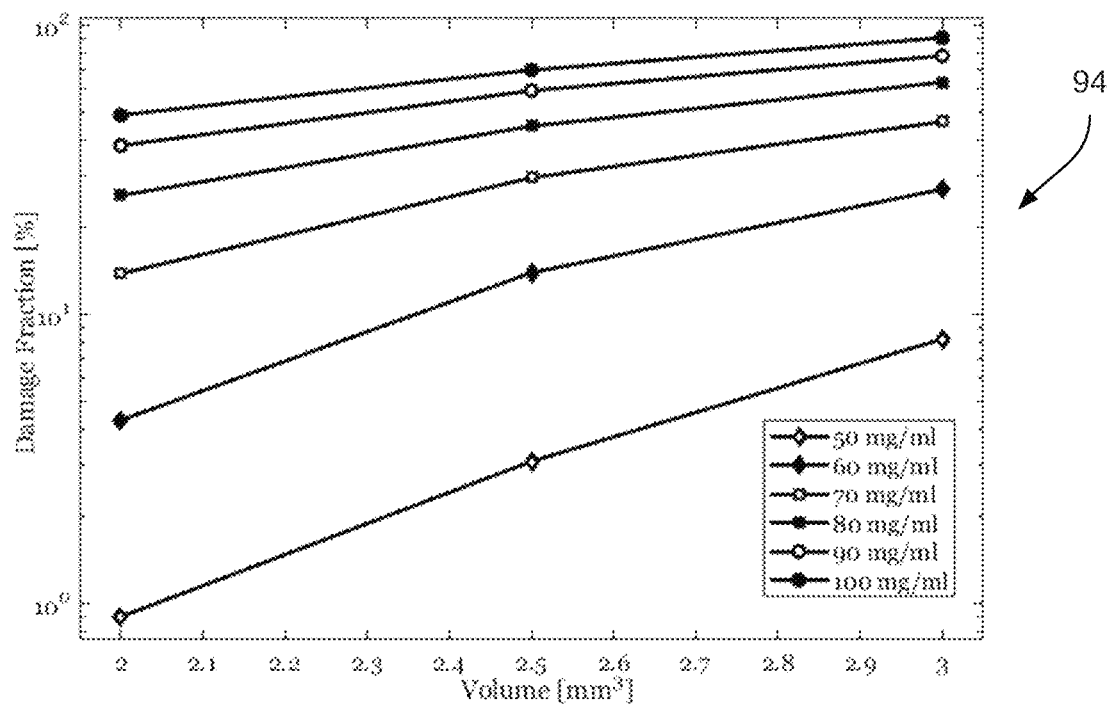
FIG. 9(b) illustrates a graph depicting data indicative of a fraction of damaged tissue for neural activation with various volume of MNP solution in 15-minute exposure, in accordance with an embodiment.

Further investigations on impacts of exposure time and the volume of MNP solution are depicted in FIG. 9(a) and FIG. 9(b). FIG. 9(a) illustrates a graph 92 depicting data indicative of the impact of various exposure time on brain tissue for 2 mm$^3$ of solution, in accordance with an embodiment. FIG. 9(b) illustrates a graph 94 depicting data indicative of a fraction of damaged tissue for neural activation with various volume of MNP solution in 15-minute exposure, in accordance with an embodiment.

For longer periods of exposure, simulation results show that the fraction of damage increases even for lower MNP concentrations. For instance, the damage fractions of 20-minute exposure for 70 mg/mL and 80 mg/mL of MNP concentrations reach 16.1% and 28.2%, respectively as can be seen in graph 92 of FIG. 9(a). However, the maximum average temperatures are 41.4° C. and 42° C., respectively which demonstrate the lack of practicality under these conditions. FIG. 9(b) demonstrates the extreme damage of targeted region for a 3 mm$^3$ solution for all concentrations excluding 50 mg/mL and 60 mg/mL. Up to this point the impacts of the decision variables in magnetothermal neuromodulation are carefully investigated. Nevertheless, the need for the best stimulation condition leading to the least damage and further efforts to find out which variable is dominant, is important. This concern motivated the disclosed inventors to employ an optimization approach to provide an optimum condition regarding the decision variables.

Figure 10:
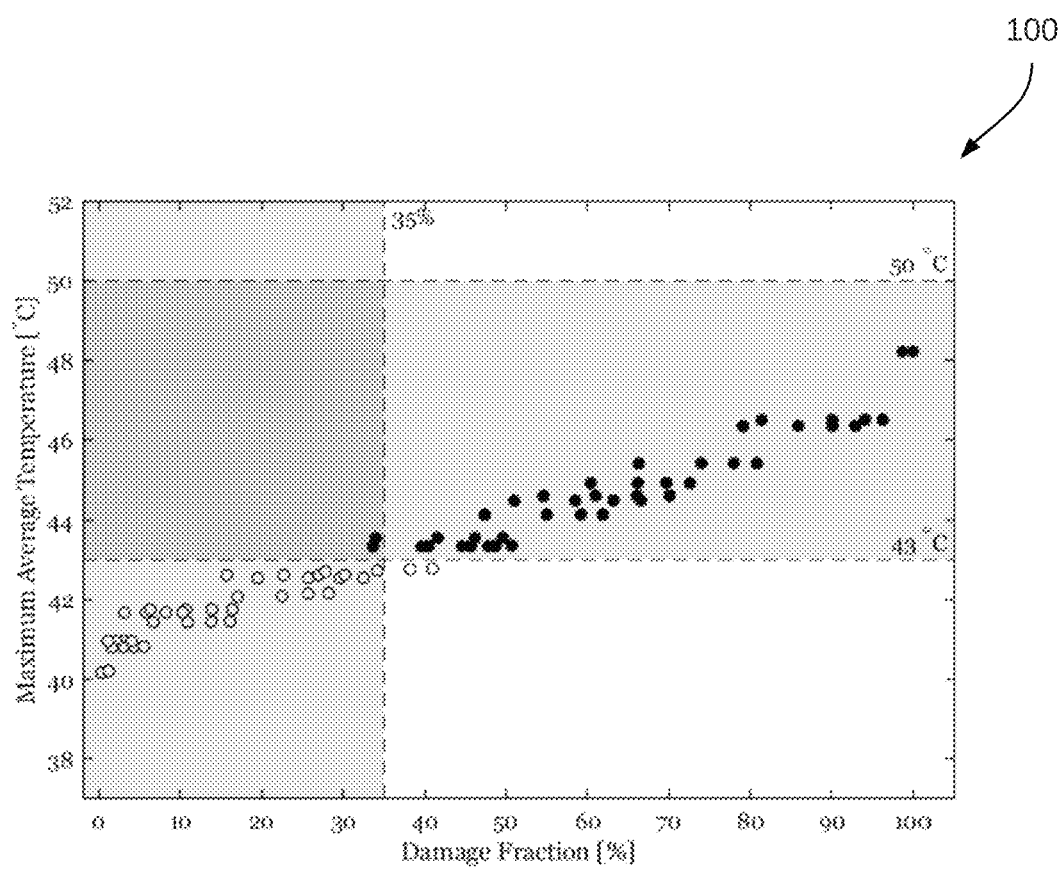
FIG. 10 illustrates a graph depicting data indicative of a damage fraction versus the highest average temperature at the end of exposure for different magnetothermal cases, in accordance with an embodiment.

FIG. 10 illustrates a graph 100 depicting data indicative of a damage fraction versus the highest average temperature at the end of exposure for different magnetothermal cases, in accordance with an embodiment. Graph 100 of FIG. 10 shows the optimization results based on the objective function and the constraint. Each point accounts for a certain value of the decision variables resulting the corresponding damage and temperature after stimulation. The gray shaded area indicates the safe temperature domain as defined earlier and the red area shows the cases with less than 35% damage.

For most of the cases with less than 35% fraction, the maximum temperature after the exposure is below 43° C. and for those that the temperature peak rises up within the domain, a significant ratio of damage can be observed. In FIG. 10, the yellow points refer to those cases that satisfy the minimum stimulation temperature, otherwise the points are in blue. (Note that although the graphs disclosed herein are presented in black and white, various colors were used in the original figures presented in the provisional application; therefore, the original colored graphs and other colored figures may be viewed in the appendices to the provisional application).

According to FIG. 10, there are only two points located in the common area of red and gray shades that effectively stimulate ion channels through magnetic transducers as well as preserving neuron cells from thermal cytotoxicity. The quantitative data of these two cases are listed in Table 2.

TABLE 2

Optimum condition for magnetothermal neuromodulation with the least thermal side effects

| Concentration [mg/ml] | Volume of MNP solution [mm$^3$] | Exposure Time [s] | Damage Fraction [%] | Max Temperature [° C.] |
|---|---|---|---|---|
| 80 | 2.5 | 300 | 33.7 | 43.3 |
| 70 | 3 | 300 | 34 | 43.5 |

Prediction of the thermal response and temperature distribution of the brain tissue when subjected to an alternating magnetic field are highly crucial for therapeutic applications. In the disclosed embodiments, a comprehensive approach, which incorporates the pertinent physical attributes such as blood perfusion, tissue conduction and metabolic heat generation can be implemented to predict the temperature response over time. Consequently, a Nelder-Mead Method optimization method can be employed to attain the efficient condition for stimulation regarding thermal cytotoxic objective function.

To avoid remote stimulation side effects and to meet stimulation minimum temperature, it may be essential to maintain the tissue affected temperature between 43° C. and 50° C. which can be considered as an inequality restriction in the optimization. Applied pulsating radiation enabled us to gradually raise the temperature to protect the biological material from the adverse thermal side effects. Contrary to the experimental results that only provide an average temperature, analysis of the temperature distribution shows that the local temperature violates the safe domain temperature. Two methods were utilized to evaluate the damaged tissue attributes. According to both approaches, in the proposed experiments, high fraction of neurons particularly around an MNP solution can endure the thermal damage. Our results suggest maintaining the small volume of solution at low levels of concentration as well as applying the AMF within a short period. Optimization results demonstrate conditions under which we can attain high performance for the ion channel activation with minimum danger to the tissue.

Figure 11:
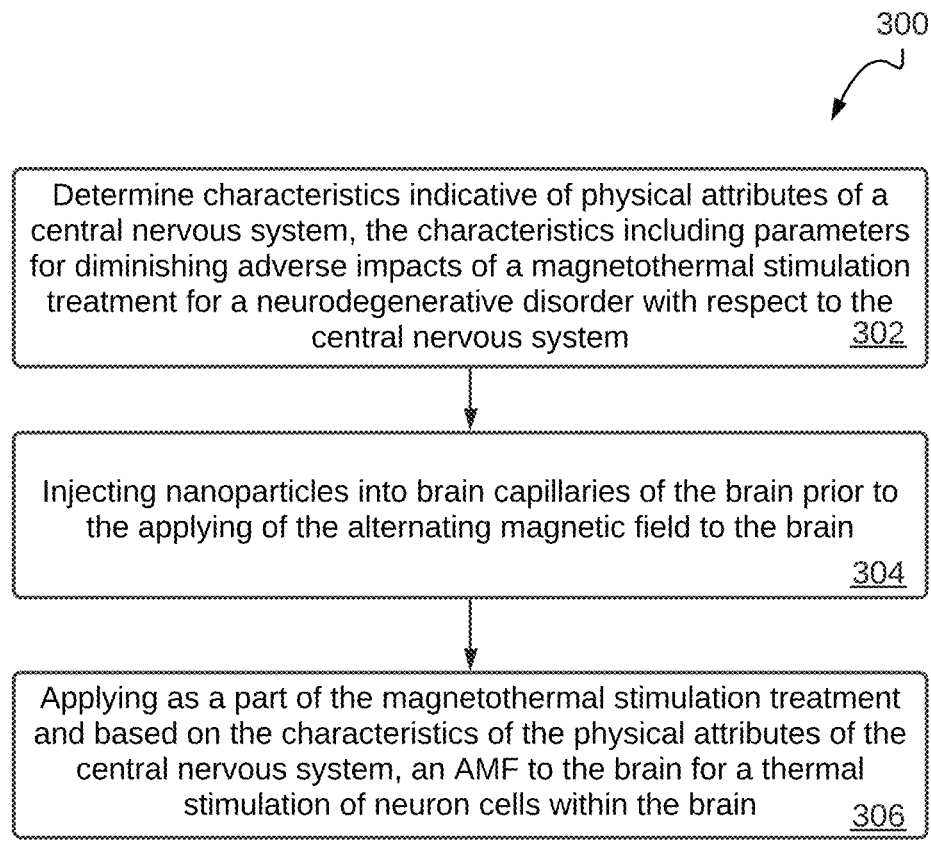
FIG. 11 illustrates a high level flow chart depicting logical operational steps of a method for noninvasively treating a neurodegenerative disorder, in accordance with an embodiment.

FIG. 11 illustrates a high level flow chart depicting logical operational steps of a method 300 for noninvasively treating a neurodegenerative disorder, in accordance with an embodiment. As shown at block 302, a step or operation can be implemented for determining characteristics indicative of physical attributes of a central nervous system. These characteristics can include parameters for diminishing the adverse impacts of the magnetothermal stimulation treatment for a neurodegenerative disorder with respect to the central nervous system. Next, as depicted at block 304, a step or operation can be implemented to inject the nanoparticles into brain capillaries of the brain prior to application of an alternating magnetic field to the brain. Note that the term nanoparticles as utilized herein can include magnetic nanoparticles (MNP), as discussed previously. Nanoparticles may include remotely-controlled nano-transducers.

Thereafter, as shown at block 306, a step or operation can be implemented to apply as a part of the disclosed magnetothermal stimulation treatment, and based on the determined characteristics of the physical attributes of the central nervous system, an alternating magnetic field to the brain for a thermal stimulation of neuron cells within the brain.

Note that the aforementioned determined characteristics indicative of the physical attributes can include, for example, one or more of: flow dynamics, magnetic nanoparticle interactions with capillary flow, heat transfer, and regulated neural signaling. In some embodiments, the aforementioned characteristics can include temperature profiles within the central nervous system when exposed to the alternating magnetic field. These characteristics can also account for the movement of ions between presynaptic cradle and astrocyte soma under an influence of a temperature elevation included in the temperature profiles. These characteristics may also include data indicative of a prediction of sodium/calcium exchanger behavior as an additional source of calcium at the presynaptic cradle as a function of an induced temperature included in the temperature profiles. Other characteristics that can be determined per the step or operation shown at block 302 can include a calculated brain tissue temperature distribution associated with the brain, wherein the calculation of the brain tissue temperature distribution can be based on a finite element method.

Figure 12:
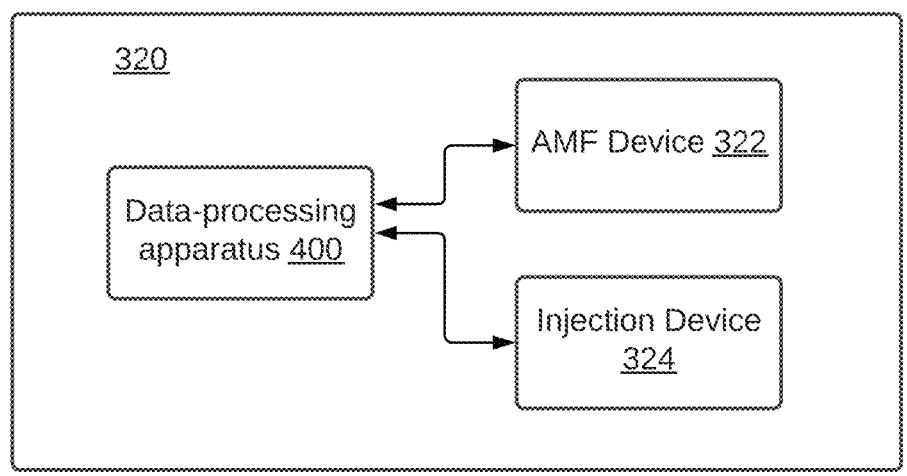
FIG. 12 illustrates a block diagram depicting a system for noninvasively treating a neurodegenerative disorder, in accordance with an embodiment.

FIG. 12 illustrates a block diagram depicting a system 320 for noninvasively treating a neurodegenerative disorder, in accordance with an embodiment. The system 320 can include, for example, a data-processing apparatus 400 (see FIG. 13 for more details of an example data-processing apparatus 400) that can determine the disclosed characteristics indicative of physical attributes of a central nervous system. As discussed, previously, such characteristics can include parameters for diminishing the adverse impacts of a magnetothermal stimulation treatment for a neurodegenerative disorder with respect to the central nervous system. The system 320 may include an AMF device (or system) 322 for applying as a part of the magnetothermal stimulation treatment and based on the characteristics of the physical attributes of the central nervous system, an alternating magnetic field to the brain for a thermal stimulation of neuron cells within the brain. In addition, the system 320 can include an injection device (or system) 324 that can be used for injecting the disclosed nanoparticles into brain capillaries of the brain prior to applying the alternating magnetic field to the brain.

In some embodiments, the injection device 324 may be implemented as part of a targeted drug delivery device/system that can deliver through an injection, nanoparticles (e.g., magnetic nanoparticles, transducers etc.) to the brain. For example, in an embodiment, the injection device 324 may be configured or may be operable to provide stepwise targeting of magnetic nanoparticles to brain capillary endothelial cells followed by transport through the blood-brain barrier (BBB) using magnetic force for targeted therapy of macromolecules to the brain.

Note that a preferred embodiment can employ an alternating magnetic field as discussed above. It should be appreciated, however, that the embodiments are not limited to the use of an AMF. That is, the embodiments can make use of a magnetic field including a magnetic signal that can be varied in terms of frequency, or, for example, a half cycle as opposed to full cycle sinusoidal waveforms. In some embodiments, variable frequencies and/or variable amplitudes can be applied based on the target patient (or based on the patient's response to the disclosed therapy). Randomization of the signal may be effective in some cases. The AMF device 322, for example, may be provided as a device that generates or uses the magnetic fields with magnetic signals that can vary in terms of frequency or amplitude or randomized as discussed above. The term 'magnetic field' as utilized herein can relate to, for example, an alternating magnetic field or a variable magnetic field and magnetic field signals thereof.

In some alternative embodiments, single polarity pulses, alternating (+/−) pulses, varying peaks, and/or varying signals for the disclosed magnetic signal treatment may be being applied during therapy. Furthermore, the time periods (e.g., 10 minute) mentioned throughout this disclosure are only examples and are not meant to limit the duration of therapy applied to patients. In addition, the various parameters, measurements, and values discussed herein are presented for exemplary purposes only and should not be considered limiting features of the embodiments.

The embodiments are described at least in part herein with reference to various graphs, flowchart illustrations and/or block diagrams of methods, systems, and computer program products and data structures according to embodiments of the invention. It will be understood that each block of the illustrations, or some blocks of the illustrations, and combinations of blocks, can be implemented by computer program instructions. These computer program instructions may be provided to a processor of, for example, a general-purpose computer, special-purpose computer, or other programmable data processing apparatus to produce a machine, such that the instructions, which execute via the processor of the computer or other programmable data processing apparatus, create means for implementing the functions/acts specified in the block or blocks.

To be clear, the disclosed embodiments can be implemented in the context of, for example a special-purpose computer or a general-purpose computer, or other programmable data processing apparatus or system. For example, in some example embodiments, a data processing apparatus or system can be implemented as a combination of a special-purpose computer and a general-purpose computer. In this regard, a system composed of different hardware and software modules and different types of features, for example, may be considered a special-purpose computer designed with the specific purpose of a medical treatment system for noninvasively treating a neurodegenerative disorder.

Embodiments may be implemented as a method, and/or a computer program product at any possible technical detail level of integration. The computer program product may include a computer readable storage medium (or media)

having computer readable program instructions thereon for causing a processor to carry out aspects of the embodiments.

The aforementioned computer program instructions may also be stored in a computer-readable memory that can direct a computer or other programmable data processing apparatus to function in a particular manner, such that the instructions (e.g., steps/operations) stored in the computer-readable memory produce an article of manufacture including instruction means which implement the function/act specified in the various block or blocks, flowcharts, and other architecture illustrated and described herein.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The flow charts and block diagrams in the figures illustrate the architecture, functionality, and operation of possible implementations of systems, methods, and computer program products according to various embodiments (e.g., preferred or alternative embodiments). In this regard, each block in the flow chart or block diagrams may represent a module, segment, or portion of instructions, which comprises one or more executable instructions for implementing the specified logical function(s).

In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The functionalities described herein may be implemented entirely and non-abstractly as physical hardware, entirely as physical non-abstract software (including firmware, resident software, micro-code, etc.) or combining non-abstract software and hardware implementations that may all generally be referred to herein as a "circuit," "module," "engine", "component," "block", "database", or "system." Furthermore, aspects of the present disclosure may take the form of a computer program product embodied in one or more non-ephemeral computer readable media having computer readable and/or executable program code embodied thereon.

Figure 13:
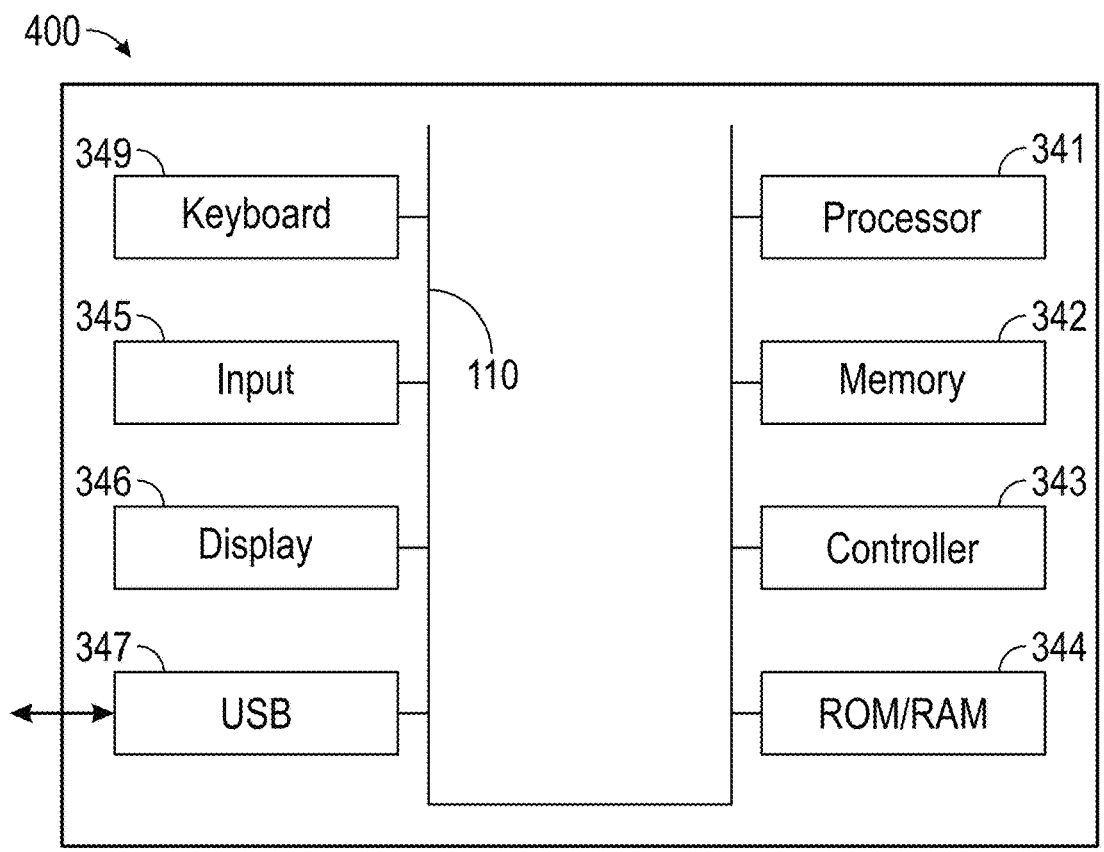
FIG. 13 illustrates a schematic view of a computer system, in accordance with an embodiment.
Figure 14:
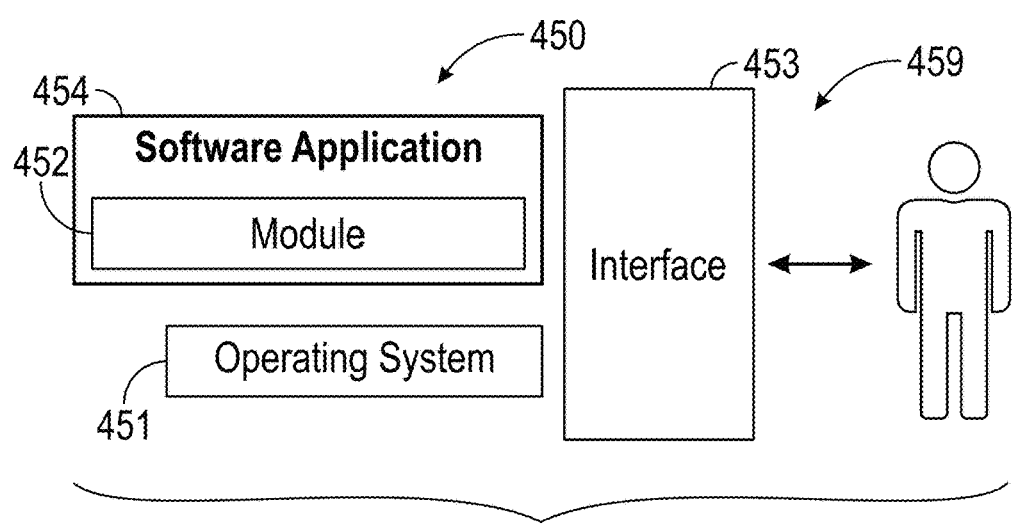
FIG. 14 illustrates a schematic view of a software system including a module, an operating system, and a user interface, in accordance with an embodiment.

FIG. 13 and FIG. 14 are shown only as exemplary diagrams of data-processing environments in which example embodiments may be implemented. It should be appreciated that FIG. 13 and FIG. 14 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 13, some embodiments may be implemented in the context of a data-processing system 400 that can include, for example, one or more processors such as a processor 341 (e.g., a CPU (Central Processing Unit) and/or other microprocessors), a memory 342, a controller 343, additional memory such as ROM/RAM 344 (i.e. ROM and/or RAM), a peripheral USB (Universal Serial Bus) connection 347, a keyboard 349 and/or another input device 345 (e.g., a pointing device, such as a mouse, track ball, pen device, etc.), a display 346 (e.g., a monitor, touch screen display, etc) and/or other peripheral connections and components.

The system bus 110 shown in FIG. 13 can serve as the main electronic information highway interconnecting the other illustrated components of the hardware of data-processing system 400. In some embodiments, the processor 341 may be a CPU that functions as the central processing unit of the data-processing system 400, performing calculations and logic operations required to execute a program. Such a CPU, alone or in conjunction with one or more of the other elements, is an example of a production device, a computing device or a processor. Read only memory (ROM) and random access memory (RAM) of the ROM/RAM 344 constitute examples of non-transitory computer-readable storage media.

The controller 343 can interface with one or more optional non-transitory computer-readable storage media to the system bus 110. These storage media may include, for example, an external or internal DVD drive, a CD ROM drive, a hard drive, flash memory, a USB drive or the like. These various drives and controllers can be optional devices. Program instructions, software or interactive modules for providing an interface and performing any querying or analysis associated with one or more data sets may be stored in, for example, ROM and/or RAM 344. Optionally, the program instructions may be stored on a tangible, non-transitory computer-readable medium such as a compact disk, a digital disk, flash memory, a memory card, a USB drive, an optical disc storage medium and/or other recording medium As illustrated, the various components of data-processing system 400 can communicate electronically through a system bus 351 or similar architecture. The system bus 351 may be, for example, a subsystem that transfers data between, for example, computer components within data-processing system 400 or to and from other data-processing devices, components, computers, etc. The data-processing system 400 may be implemented in some embodiments as, for example, a server in a client-server based network (e.g., the Internet) or in the context of a client and a server (i.e., where aspects are practiced on the client and the server).

In some example embodiments, data-processing system 400 may be, for example, a standalone desktop computer, a laptop computer, a Smartphone, a pad computing device and so on, wherein each such device can be operably connected to and/or in communication with a client-server based network or other types of networks (e.g., cellular networks, Wi-Fi, etc).

FIG. 14 illustrates a computer software system 450 for directing the operation of the data-processing system 400 depicted in FIG. 13. The software application 454, stored for example in memory 342 and/or another memory, generally includes one or more modules such as module 452. The computer software system 450 also includes a kernel or operating system 451 and a shell or interface 453. One or more application programs, such as software application 454, may be "loaded" (i.e., transferred from, for example, mass storage or another memory location into the memory 342) for execution by the data-processing system 400. The data-processing system 400 can receive user commands and data through the interface 453; these inputs may then be acted upon by the data-processing system 400 in accordance with instructions from operating system 451 and/or software application 454. The interface 453 in some embodiments can serve to display results, whereupon a user 459 may supply additional inputs or terminate a session. The software application 454 can include module(s) 452, which can, for example, implement the various methods, models, steps, instructions or operations such as those discussed herein.

The following discussion is intended to provide a brief, general description of suitable computing environments in which the system and method may be implemented. Although not required, the disclosed embodiments will be described in the general context of computer-executable instructions, such as program modules, being executed by a single computer. In most instances, a "module" (also referred to as an "engine") may constitute a software application, but can also be implemented as both software and hardware (i.e., a combination of software and hardware).

Generally, program modules include, but are not limited to, routines, subroutines, software applications, programs, objects, components, data structures, etc., that perform particular tasks or implement particular data types and instructions. Moreover, those skilled in the art will appreciate that the disclosed method and system may be practiced with other computer system configurations, such as, for example, hand-held devices, multi-processor systems, data networks, microprocessor-based or programmable consumer electronics, networked PCs, minicomputers, mainframe computers, servers, and the like.

Note that the term module as utilized herein can relate to a collection of routines and data structures that perform a particular task or implements a particular data type. Modules may be composed of two parts: an interface, which lists the constants, data types, variable, and routines that can be accessed by other modules or routines, and an implementation, which is typically private (accessible only to that module) and which includes source code that actually implements the routines in the module. The term module may also simply refer to an application, such as a computer program designed to assist in the performance of a specific task, such as word processing, accounting, inventory management, etc.

In some example embodiments, the term "module" can also refer to a modular hardware component or a component that is a combination of hardware and software. It should be appreciated that implementation and processing of such modules according to the approach described herein can lead to improvements in processing speed and ultimately in energy savings and efficiencies in a data-processing system such as, for example, the data-processing system 400. A "module" can perform the various steps, operations or instructions of the methods discussed herein.

FIG. 13 and FIG. 14 are intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including Macintosh, UNIX, LINUX, and the like.

It is understood that the specific order or hierarchy of steps, operations, or instructions in the processes or methods disclosed is an illustration of exemplary approaches. For example, the various steps, operations or instructions discussed herein can be performed in a different order. Similarly, the various steps and operations of the disclosed example pseudo-code discussed herein can be varied and processed in a different order. Based upon design preferences, it is understood that the specific order or hierarchy of such steps, operation or instructions in the processes or methods discussed and illustrated herein may be rearranged. The accompanying claims, for example, present elements of the various steps, operations or instructions in a sample order, and are not meant to be limited to the specific order or hierarchy presented.

The inventors have realized a non-abstract technical solution to the technical problem to improve an underlying medical technology by improving efficiencies in such medical treatment technologies. The disclosed embodiments offer technical improvements to a medical treatment technology including non-abstract improvements to the technical problem(s) identified in the background section of this disclosure. The ability to determine the characteristics indicative of physical attributes of a central nervous system that can diminish the adverse impacts of a magnetothermal stimulation treatment for a neurodegenerative can result in increased efficiencies and successes in the application of magnetothermal stimulation treatments with an alternating magnetic field to the brain for a thermal stimulation of neuron cells within the brain. For example, application of the disclosed optimization methods can be employed to attain efficient conditions for stimulation regarding the disclosed thermal cytotoxic objective function.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method for noninvasively treating a neurodegenerative disorder with a medical treatment system, the method comprising:

determining characteristics of physical attributes of a central nervous system that diminish adverse impacts of a medical magnetothermal stimulation treatment for a neurodegenerative disorder with respect to the central nervous system, the medical magnetothermal stimulation treatment comprising a thermal stimulation of targeted neural circuits of the central nervous system with remotely controlled nano-transducers; and applying as a part of the medical magnetothermal stimulation treatment and based on the characteristics of the physical attributes of the central nervous system, a magnetic field to a brain associated with the central nervous system for the thermal stimulation of the targeted neural circuits comprising neuron cells within the brain, wherein the characteristics of the physical attributes of the central nervous system comprise at least one of: blood flow dynamics, magnetic nanoparticle interactions with capillary flow, heat transfer, and regulated neural signaling.

2. The method of claim 1, wherein the magnetic field is applied to the brain as a part of the medical magnetothermal stimulation treatment as stimulation pulses to maintain a tissue temperature associated with the brain or the central nervous system within a benign temperature domain.

3. The method of claim 2, wherein the benign temperature domain comprises a temperature range between 43° C. and 50° C.

4. The method of claim 3, wherein the magnetic field comprises at least one of: an alternating magnetic field or a variable magnetic field and magnetic signals associated with the magnetic field.

5. The method of claim 1, wherein a frequency of a magnetic signal associated with the magnetic field is varied as a part of the medical magnetothermal stimulation treatment.

6. The method of claim 1, further comprising delivering nanoparticles into brain capillaries of the brain prior to applying of the magnetic field to the brain, wherein delivering of the nanoparticles into the brain capillaries comprises stepwise targeting of the nanoparticles to brain capillary endothelial cells of the brain followed by transport through a blood-brain barrier (BBB) of the brain using a magnetic force for a targeted therapy of macromolecules to the brain, the nanoparticles comprising the remotely controlled nano-transducers.

7. The method of claim 1, further comprising delivering nanoparticles comprising the remotely controlled nano-transducers into brain capillaries of the brain with a targeted drug delivery device prior to the applying of the magnetic field to the brain.

8. The method of claim 1, wherein the characteristics of the physical attributes further comprise temperature profiles within the central nervous system when exposed to the magnetic field.

9. The method of claim 8, further comprising calculating a brain tissue temperature distribution associated with the brain based on a finite element method.

10. The method of claim 8, wherein the characteristics of the physical attributes account for a movement of ions between a presynaptic cradle and astrocyte soma under an influence of a temperature elevation included in the temperature profiles.

11. The method of claim 8, wherein the characteristics comprise data indicative of a prediction of sodium/calcium exchanger behavior as an additional source of calcium at a presynaptic cradle as a function of an induced temperature included in the temperature profiles.

12. The method of claim 1 wherein the neurodegenerative disorder comprises Alzheimer's disease.

13. The method of claim 1 wherein the neurodegenerative disorder comprises Parkinson's disease.

14. A method for noninvasively treating a neurodegenerative disorder with a medical treatment system, the method comprising:
   determining characteristics of physical attributes of a central nervous system that diminish adverse impacts of a medical magnetothermal stimulation treatment for a neurodegenerative disorder with respect to the central nervous system, the medical magnetothermal stimulation treatment comprising a thermal stimulation of targeted neural circuits of the central nervous system with remotely controlled nano-transducers;
   applying as a part of the medical magnetothermal stimulation treatment and based on the characteristics of the physical attributes of the central nervous system, a magnetic field to a brain associated with the central nervous system for the thermal stimulation of the targeted neural circuits comprising neuron cells within the brain, wherein the characteristics of the physical attributes further comprise temperature profiles within the central nervous system when exposed to the magnetic field; and
   calculating a brain tissue temperature distribution associated with the brain based on a finite element method.

15. The method of claim 14 wherein the neurodegenerative disorder comprises Alzheimer's disease.

16. The method of claim 14 wherein the neurodegenerative disorder comprises Parkinson's disease.

17. A method for noninvasively treating a neurodegenerative disorder with a medical treatment system, the method comprising:
   determining characteristics of physical attributes of a central nervous system that diminish adverse impacts of a medical magnetothermal stimulation treatment for a neurodegenerative disorder with respect to the central nervous system, the medical magnetothermal stimulation treatment comprising a thermal stimulation of targeted neural circuits of the central nervous system with remotely controlled nano-transducers;
   applying as a part of the medical magnetothermal stimulation treatment and based on the characteristics of the physical attributes of the central nervous system, a magnetic field to a brain associated with the central nervous system for the thermal stimulation of the targeted neural circuits comprising neuron cells within the brain, wherein the characteristics of the physical attributes account for a movement of ions between a presynaptic cradle and astrocyte soma under an influence of a temperature elevation included in temperature profiles.

18. The method of claim 17 wherein the neurodegenerative disorder comprises at least one of: Alzheimer's disease or Parkinson's disease.

19. The method of claim 17, further comprising delivering nanoparticles into brain capillaries of the brain prior to applying of the magnetic field to the brain, wherein delivering of the nanoparticles into the brain capillaries comprises stepwise targeting of the nanoparticles to brain capillary endothelial cells of the brain followed by transport through a blood-brain barrier (BBB) of the brain using a magnetic force for a targeted therapy of macromolecules to the brain, the nanoparticles comprising the remotely controlled nano-transducers.

20. The method of claim 17, further comprising delivering nanoparticles comprising the remotely controlled nano-transducers into brain capillaries of the brain with a targeted drug delivery device prior to the applying of the magnetic field to the brain.

* * * * *